United States Patent
Oliphant et al.

(10) Patent No.: US 9,640,374 B2
(45) Date of Patent: May 2, 2017

(54) DECONVOLUTION AND IDENTIFICATION ALGORITHMS FOR USE ON SPECTROSCOPIC DATA

(71) Applicant: TORION TECHNOLOGIES, INC., American Fork, UT (US)

(72) Inventors: Joseph L. Oliphant, Highland, UT (US); Chad B. Grant, Saratoga Springs, UT (US); H. Dennis Tolley, Mapleton, UT (US)

(73) Assignee: TORION TECHNOLOGIES, INC., American Fork, UT (US)

( * ) Notice: Subject to any disclaimer, the term of this patent is extended or adjusted under 35 U.S.C. 154(b) by 996 days.

(21) Appl. No.: 13/793,555

(22) Filed: Mar. 11, 2013

(65) Prior Publication Data

US 2013/0238253 A1     Sep. 12, 2013

Related U.S. Application Data

(60) Provisional application No. 61/609,118, filed on Mar. 9, 2012.

(51) Int. Cl.
*H01J 49/00*     (2006.01)
*G01N 30/86*     (2006.01)

(52) U.S. Cl.
CPC ...... *H01J 49/0036* (2013.01); *G01N 30/8679* (2013.01)

(58) Field of Classification Search
CPC .............. G01N 30/86; G01N 30/8679; G01N 30/8696; G01N 30/8675; G01N 30/8617;
(Continued)

(56) References Cited

U.S. PATENT DOCUMENTS 5,273,632 A * 12/1993 Stockham ........ G01N 27/44717
                                                    204/450
5,453,613 A * 9/1995 Gray ..................... H01J 49/025
                                                    250/281
(Continued)

FOREIGN PATENT DOCUMENTS

WO       2008035959 A1     3/2008

OTHER PUBLICATIONS

S.E. Stein, An integrated method for spectrum extraction and compound identification from gas chromatography/mass spectrometry data, Journal of the American Society for Mass Spectrometry, vol. 10, Issue 8, Aug. 1999, pp. 770-781.
(Continued)

*Primary Examiner* — Nicole Ippolito
*Assistant Examiner* — Sean Luck
(74) *Attorney, Agent, or Firm* — Morriss O'Bryant Compagni, PC

(57) ABSTRACT

A new algorithm is taught for identifying compounds from spectroscopic or mass spectra data, wherein the improved order of operations of the present invention are defined as 1) background noise removal, 2) deconvolution by smoothing peaks, finding peaks and grouping peaks into unknown compounds, 3) preparing correlation values for combinations of unknown compound and target compound pairs, 4) sorting the combinations of unknown compound and target compound pairs by their correlation values, 5) removing complete ions from the mass spectra data using a peak, a retention time, and a retention window, and 6) matching unknown compounds to target compounds such that no target compound appears twice.

17 Claims, 38 Drawing Sheets

(58) Field of Classification Search
CPC ............. G01N 30/862; G01N 30/8624; G01N 30/8631; H01J 49/0036
See application file for complete search history.

(56) References Cited

U.S. PATENT DOCUMENTS

| | | | | |
|---|---|---|---|---|
| 5,748,491 | A * | 5/1998 | Allison | G06K 9/00503 702/190 |
| 6,675,104 | B2 * | 1/2004 | Paulse | H01J 49/0036 702/22 |
| 7,386,173 | B1 * | 6/2008 | Kaminski | G06K 9/0053 382/207 |
| 2003/0014428 | A1 * | 1/2003 | Mascarenhas | G06F 17/30011 |
| 2003/0052263 | A1 | 3/2003 | Kaufman | |
| 2005/0114042 | A1 * | 5/2005 | Pappin | H01J 49/0036 702/30 |
| 2005/0255606 | A1 * | 11/2005 | Ahmed | G06K 9/00503 436/173 |
| 2005/0258357 | A1 * | 11/2005 | Oliphant | G06K 9/00503 250/282 |
| 2005/0288872 | A1 | 12/2005 | Old | |
| 2007/0278395 | A1 | 12/2007 | Gorenstein | |
| 2008/0020939 | A1 | 1/2008 | Stanton | |
| 2009/0294645 | A1 * | 12/2009 | Gorenstein | G06F 19/703 250/282 |

OTHER PUBLICATIONS

Hongmei Lu et al., Comparative evaluation of software for deconvolution of metabolomics data based on GC-TOF-MS, Trends in Analytical Chemistry, vol. 27, No. 3, 2008, pp. 215-227.

Christian Zeigler et al., Total alkylated polycyclic aromatic hydrocarbon characterization and quantitative comparison of selected ion monitoring versus full scan gas chromatography/mass spectrometry based on spectral deconvolution, Journal of Chromatography A, 1205 (2008) pp. 109-116.

* cited by examiner

| Smoothing Parameter | Calculated Retention Time |
|---|---|
| 3 | 53.461, 53.595 |
| 4 | 53.549 |
| 5.5 | 53.547 |
| 7 | 53.539 |
| 10 | 53.551 |
| 15 | 53.537 |
| 20 | 53.582 |

FIGURE 19

Partial List of Found Mass Peaks at Retention Time = ~53

```
Peak Number  ret.time  mass  intensity
[374,]       52.527    281   173.19582
[375,]       53.385    183   254.85501
[376,]       53.397    79    513.79071
[377,]       53.400    104   566.73465
[378,]       53.438    268   229.33027
[379,]       53.461    266   827.58682
[380,]       53.471    187   411.01563
[381,]       53.475    93    182.84856
[382,]       53.475    264   900.14322
[383,]       53.478    185   989.41029
[384,]       53.490    262   291.57918
[385,]       53.529    79    905.37722
[386,]       53.536    81    863.56126
[387,]       53.559    183   443.30834
[388,]       53.563    264   869.74308
[389,]       53.567    106   635.54721
[390,]       53.588    104   689.42372
[391,]       53.595    266   1014.47156
[392,]       53.603    93    192.01323
[393,]       53.604    268   221.11971
[394,]       53.697    262   164.60415
[395,]       53.728    268   131.61190
```

FIGURE 21

Partial List of Found Mass Peaks at Retention Time = ~53 After Bug Fix

| Peak Number | ret.time | mass | intensity |
|---|---|---|---|
| [185,] | 52.712 | 282 | 4.590577e+00 |
| [186,] | 53.511 | 262 | 1.966993e+02 |
| [187,] | 53.522 | 187 | 3.303654e+02 |
| [188,] | 53.525 | 185 | 8.182394e+02 |
| [189,] | 53.528 | 79 | 6.222656e+02 |
| [190,] | 53.528 | 104 | 5.609871e+02 |
| [191,] | 53.528 | 268 | 1.680187e+02 |
| [192,] | 53.529 | 183 | 3.216239e+02 |
| [193,] | 53.530 | 264 | 7.738259e+02 |
| [194,] | 53.536 | 106 | 5.004550e+02 |
| [195,] | 53.539 | 81 | 7.330283e+02 |
| [196,] | 53.539 | 266 | 7.557478e+02 |
| [197,] | 53.562 | 93 | 1.550536e+02 |

FIGURE 26

DECONVOLUTION AND IDENTIFICATION ALGORITHMS FOR USE ON SPECTROSCOPIC DATA

BACKGROUND OF THE INVENTION

Field of the Invention

This invention relates generally to the process of processing mass spectra data from a sample, and then identifying known compounds and collecting mass spectra data on unknown compounds for identification purposes using reference libraries of mass spectra data.

Description of Related Art

There are many devices designed for chemical analysis. One such useful device is a gas chromatography/mass spectrometry (GC/MS) system. The GC/MS system and other similar devices are used in analyzing and identifying compounds. During this analysis process, a large data file can be generated that represents the mass spectra of the various compounds in a sample being analyzed.

Many algorithms and commercial products have been developed to convert the mass spectra data file into identified compounds. One such program is known as the Automated Mass Spectral Deconvolution and Identification System (AMDIS). AMDIS extracts the spectrum of each component in a mixture of compounds that is analyzed by a GC/MS or a liquid chromatography/mass spectrometry (LC/MS) system and then identifies target compounds. The program operates by extracting pure component spectra from complex chromatograms, and then determines if the component is contained within a reference library.

While the algorithms used by AMDIS are useful, the specific algorithms and the order in which those algorithms are applied to mass spectra data does not always provide the most accurate identification of compounds for all situations. Accordingly, it would be an improvement over the prior art to provide an improved order of operation as well as refined algorithms in order to improve compound identification from mass spectra data.

BRIEF SUMMARY OF THE INVENTION

In a first embodiment of the present invention, a new algorithm is taught for identifying compounds from mass spectra data, wherein the improved order of operations of the present invention are defined as 1) background noise removal, 2) deconvolution by smoothing peaks, finding peaks and grouping peaks into unknown compounds, 3) preparing correlation values for combinations of unknown compound and target compound pairs, 4) sorting the combinations of unknown compound and target compound pairs by their correlation values, 5) removing complete ions from the mass spectra data using a peak, a retention time, and a retention window, and 6) matching unknown compounds to target compounds such that no target compound appears twice.

These and other objects, features, advantages and alternative aspects of the present invention will become apparent to those skilled in the art from a consideration of the following detailed description taken in combination with the accompanying drawings.

BRIEF DESCRIPTION OF THE SEVERAL VIEWS OF THE DRAWINGS

FIG. 19 is a table showing smoothing parameters and the corresponding calculated retention time for Mass 266.

FIGS. 20 through 38 are graphs that demonstrate various results of de-convolution for the first embodiment.

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

A new algorithm is taught for identifying compounds from spectroscopic or mass spectra data. The new algorithm may be executed by a computing device having memory for storing data and results of computations. The computing device may include the necessary processor power and peripheral access in order to store data, retrieve data and process data. The computing device may be part of a GC/MS analyzer that is used to generate spectroscopic or mass spectra data.

Figure 1:
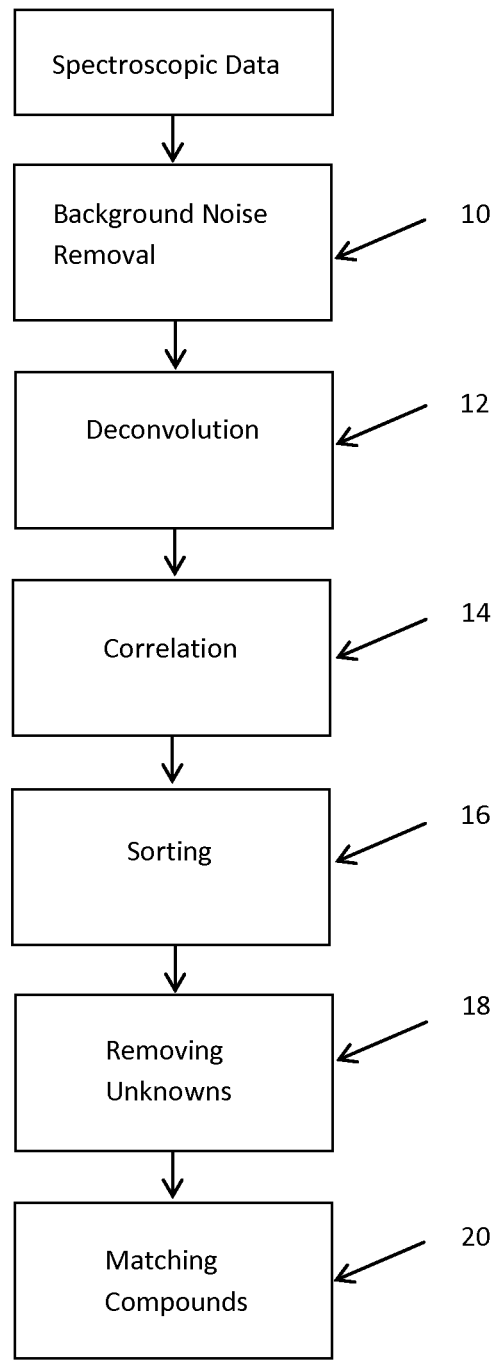
FIG. 1 is a flowchart showing the order of operations of the first embodiment of the present invention.

The first embodiment of the present invention is shown as a flowchart in FIG. 1. A typical input to the algorithm is spectroscopic data for compounds that are mixed together in a sample that has been processed by some chemical analysis device. It should not be considered a limiting factor that the data that is shown in this document is obtained from a GC/MS system and is comprised of mass spectra data, as the spectroscopic data can be obtained from any appropriate source.

The first step of the first embodiment of the present invention is to perform background noise removal 10. This first step may be a critical component of the present invention and one which substantially distinguishes the present invention from the prior art. By removing noise from the mass spectra data before analysis begins, the system is not trying to perform analysis on the noise in later steps, as is often the case in the prior art. Background noise removal operates on the principal that a signal that has a wavelength that is significantly longer than a typical chromatographic peak may contain background noise, and should not be considered part of a real signal. Consequently, the background noise is removed before analysis is performed so that analysis is being performed on cleaner mass spectra.

Background noise removal may be performed to smooth signals over a broad span so that short duration changes in signal are not fitted when performing analysis. Background noise removal may also be performed on a mass-by-mass basis, so that masses having high background signals do not interfere with masses that have low background signals Accordingly, the first embodiment of the present invention uses a low-pass filter to remove all of the chromatographic peaks of a given mass or reconstructed ion chromatogram (RIC). The data that is remaining may be multiplied by a weighting value (cutoff weight—typically 3) and then a constant may be added (cutoff threshold—typically 10) to create a threshold line for a particular mass. Values in the original data equal to or below the threshold may be set to zero, while all other values may be left unchanged.

It is noted that in order to improve the speed of the analysis, masses in which not more than 5% of their scans have a non-zero value may immediately be assumed to have a threshold of just the constant (cutoff threshold).

In more specific terms, the present invention may perform background noise removal using any method that performs the desired function. Several embodiments are now described that perform differently from each other.

In a first embodiment for background noise removal, the first step may be to divide the RIC into a number of equal subdivisions. For illustration purposes only, a subdivision representing 10 seconds of time may be selected. However, this subdivision of time is for illustration purposes only and should not be considered to be limiting.

The next step is to calculate the average time, the mean intensity, and the mean of all non-zero intensities of each subdivision. The next step is to calculate the median of all subdivision's means, and then calculate the median absolute deviation (MAD) of all subdivision's means. The first embodiment may then remove any subdivision whose mean is above the median mean plus the "MAD", or whose mean is zero. The first embodiment may then interpolate a low-pass filter value by using the average time, and mean of non-zero intensities of all remaining subdivisions. The embodiment may use the value of the non-zero intensity mean of the first remaining subdivision for all times before the first average time, and then use the value of the non-zero intensity mean of the last remaining subdivision for all the times after the last average time.

A second embodiment for performing background noise removal is also described. In the second embodiment, it may be possible to use a Locally Weighted Scatterplot Smoothing (Lowess) filter set with a fairly large span such as a span of 0.1, which is using a window that is about 10% of the data for each point considered on all the data. It was determined that including the zeros tended to pull the threshold so low that even when multiplying and adding a constant may still not produce a result that was above legitimate noise for some masses.

In a third embodiment of the present invention, it is possible to again use the Lowess filter set with a fairly large span of 0.1, but this time using non-zero data points only. This third background noise removal embodiment may give a threshold that is a much better representation of the actual noise than the second embodiment. However, on masses that have numerous peaks, the Lowess filter may also have a tendency to go unstable and be much higher than it should. This may result in important peaks being removed. Accordingly, the preferred embodiment for background noise removal is the first embodiment.

The following figures are representative of mass spectra data that may demonstrate the principles of the present invention, and should not be considered as limiting in regards to results of the embodiments.

Figure 3:
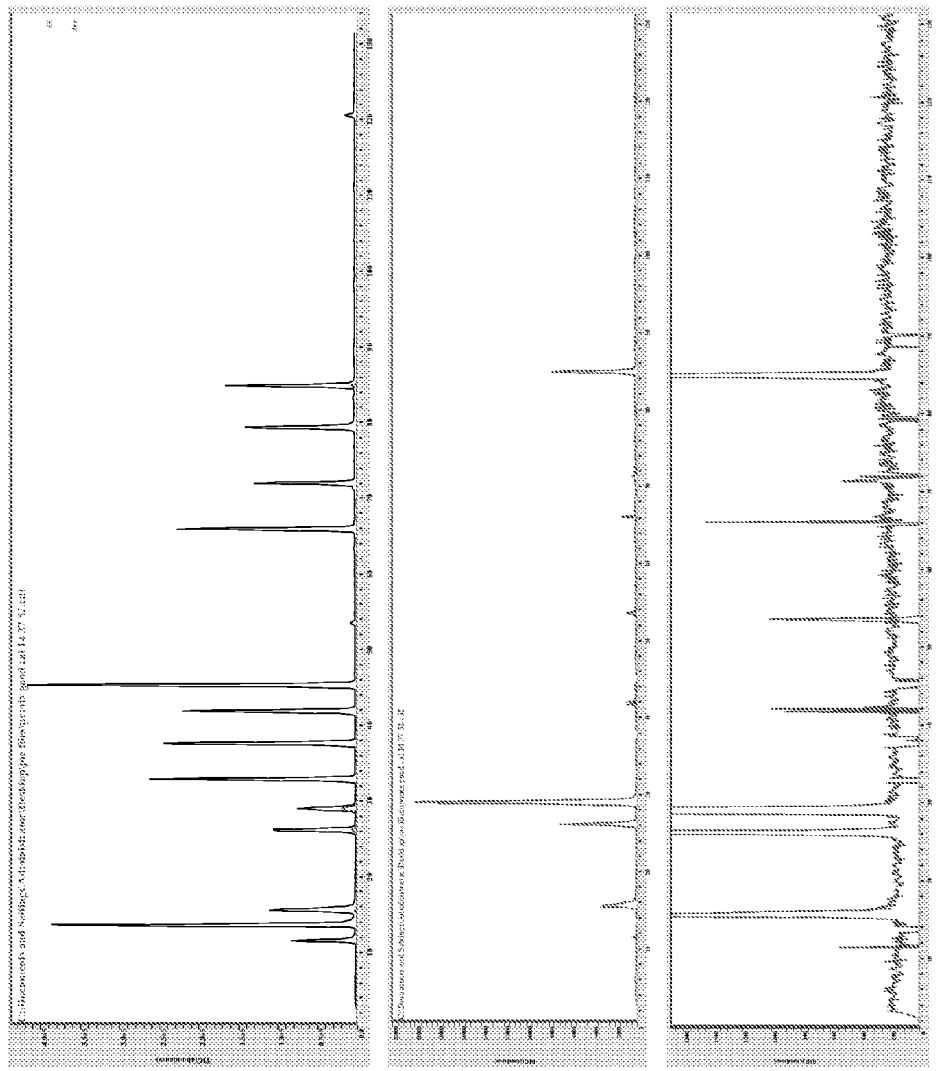
FIG. 3 shows mass spectra from a Standard 13 mix sample, where Black represents Tic, Red represents Mass 55, and Blue represents Mass 266.
Figure 4:
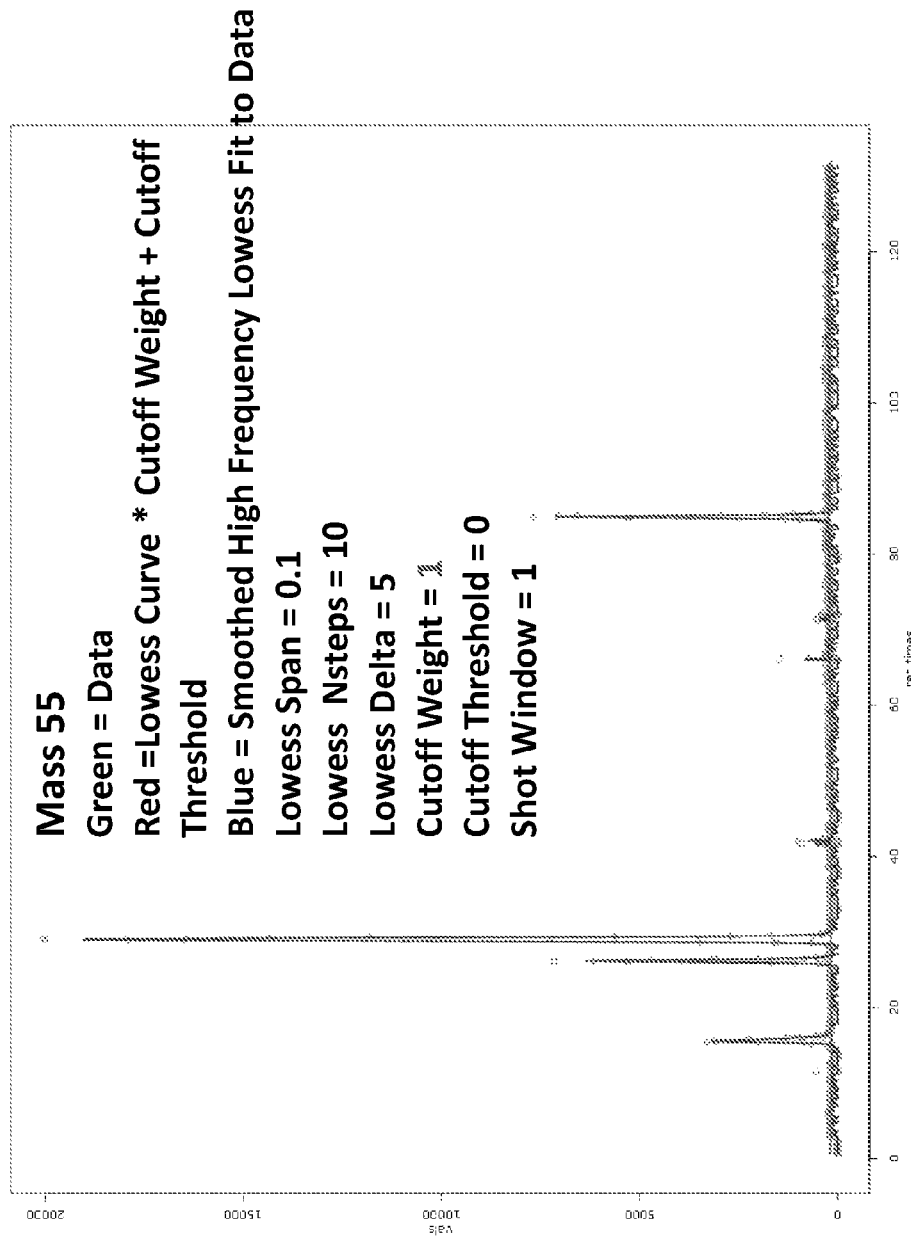
FIGS. 4 through 7 are graphs of mass spectra data for Mass 55, where Lowess parameters are changed to demonstrate the principles of operation of the first embodiment.
Figure 5:
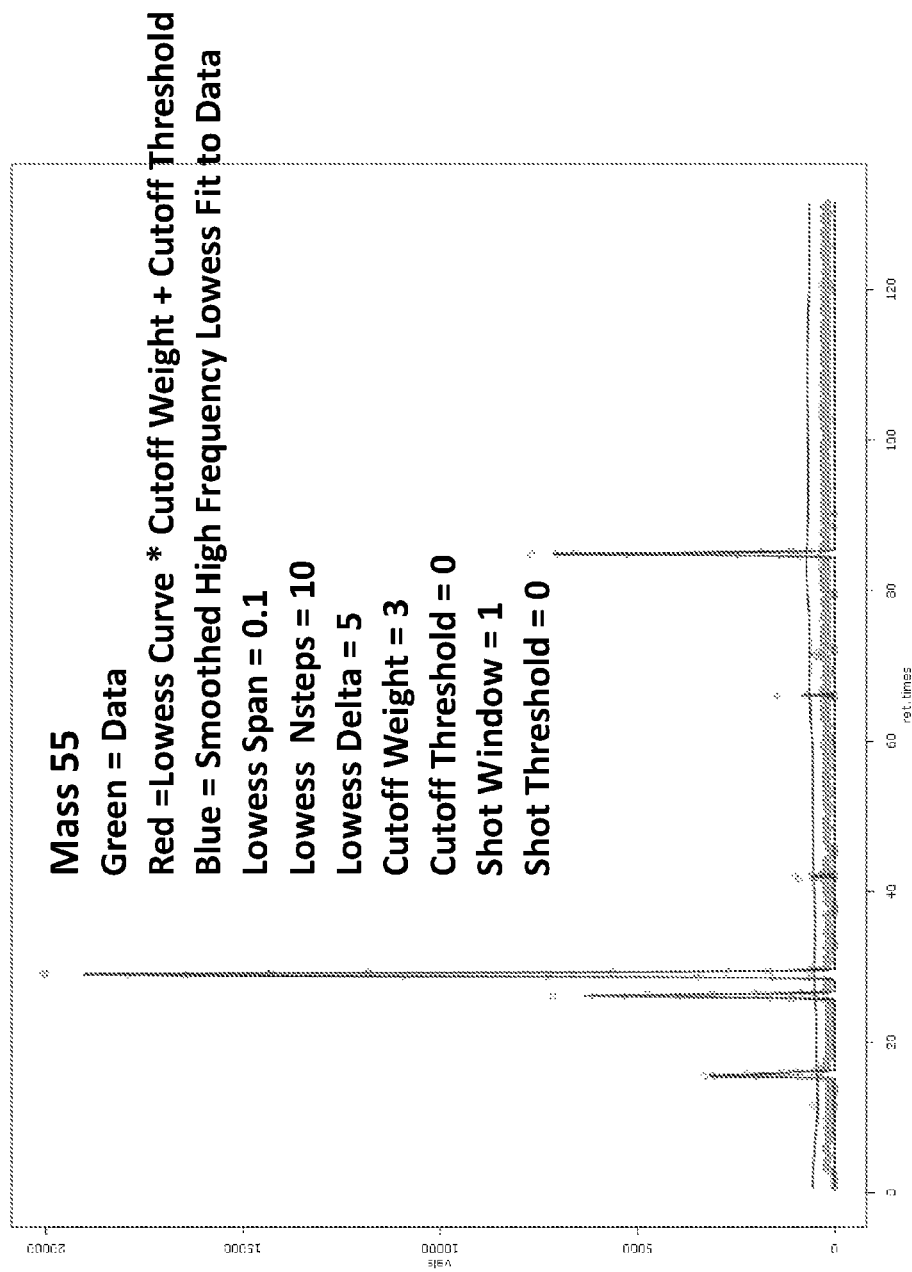
Figure 6:
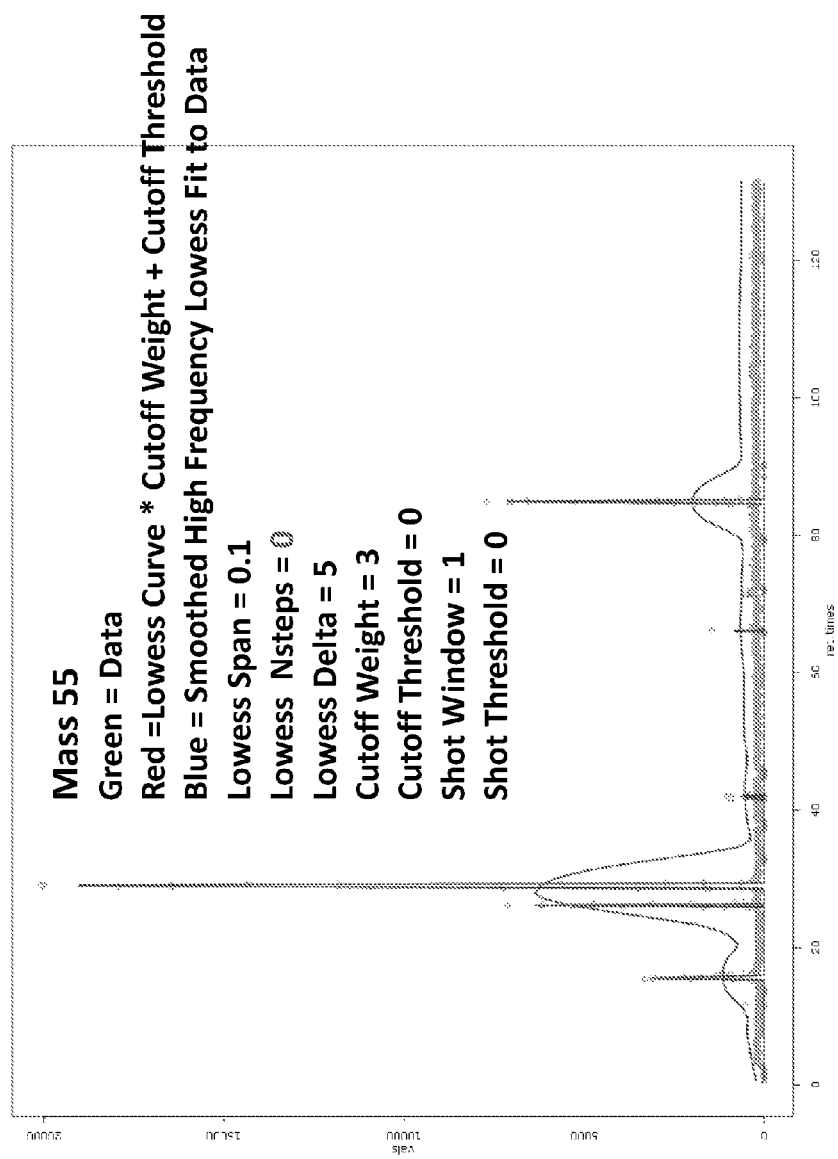
Figure 7:
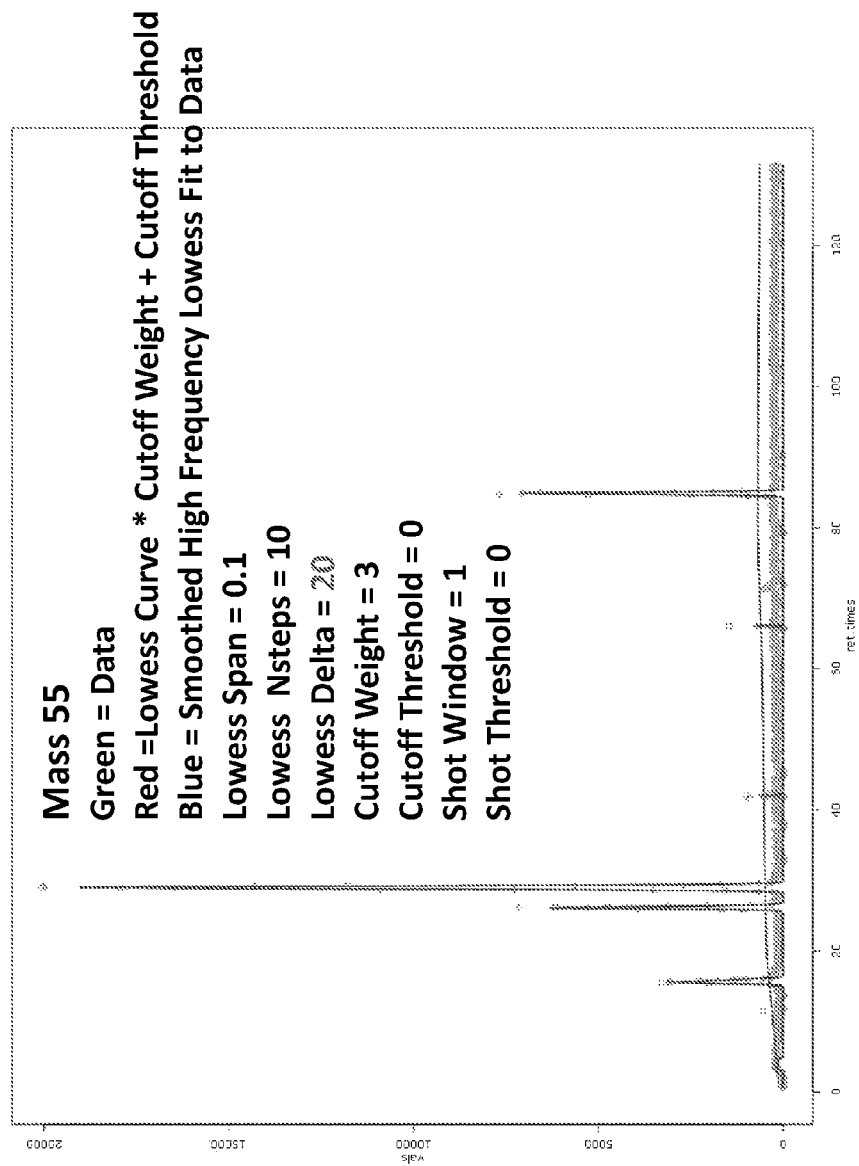

FIG. 3 shows mass spectra from a Standard 13 mix sample, where Black represents Tic, Red represents Mass 55, and Blue represents Mass 266.

FIGS. 4 through 7 are graphs that show mass spectra data for Mass 55, where Lowess parameters are changed in each figure in order to demonstrate the principles of operation of the embodiments.

Figure 8:
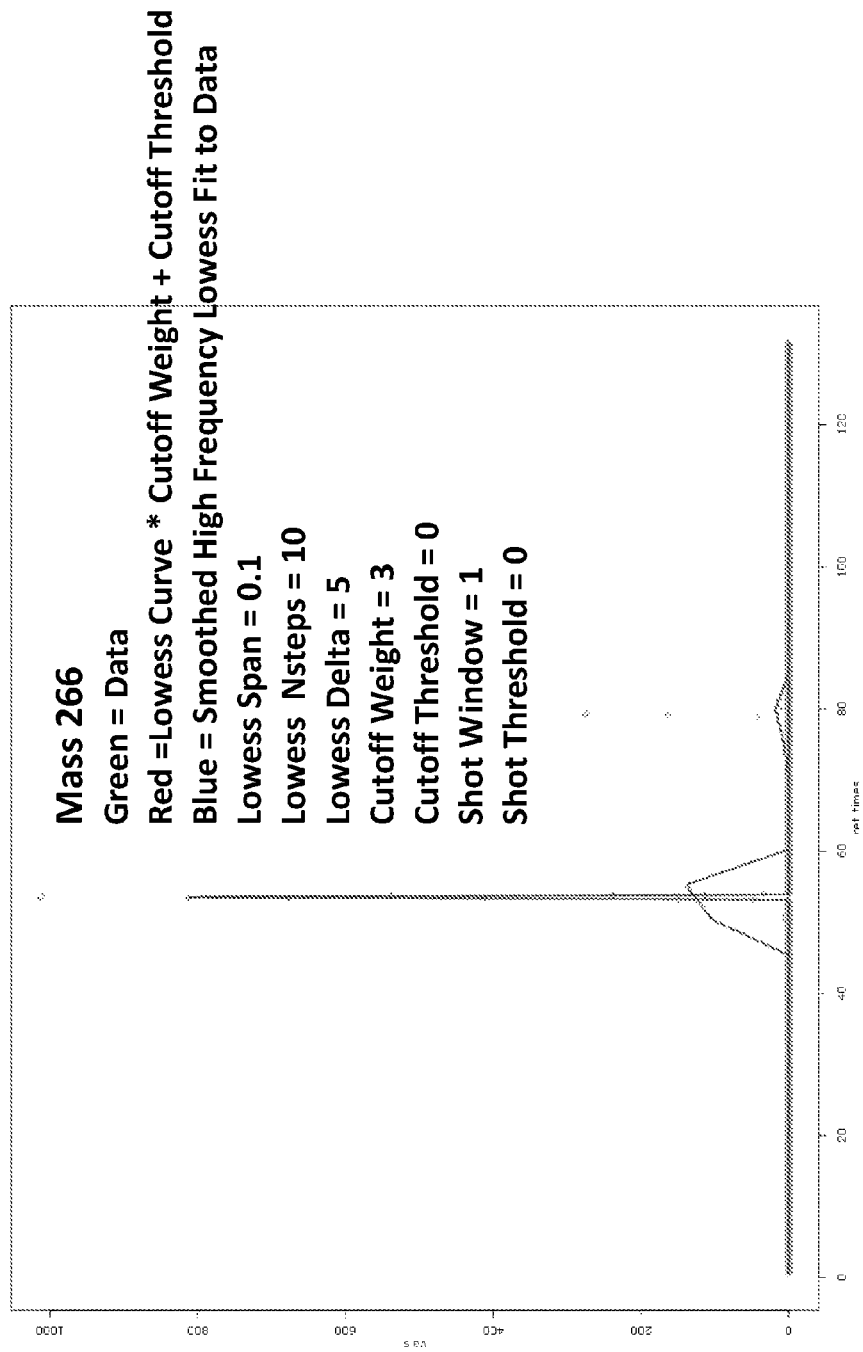
FIGS. 8 through 10 graphs of mass spectra data for Mass 266, where Lowess parameters are changed to demonstrate the principles of operation of the first embodiment.
Figure 9:
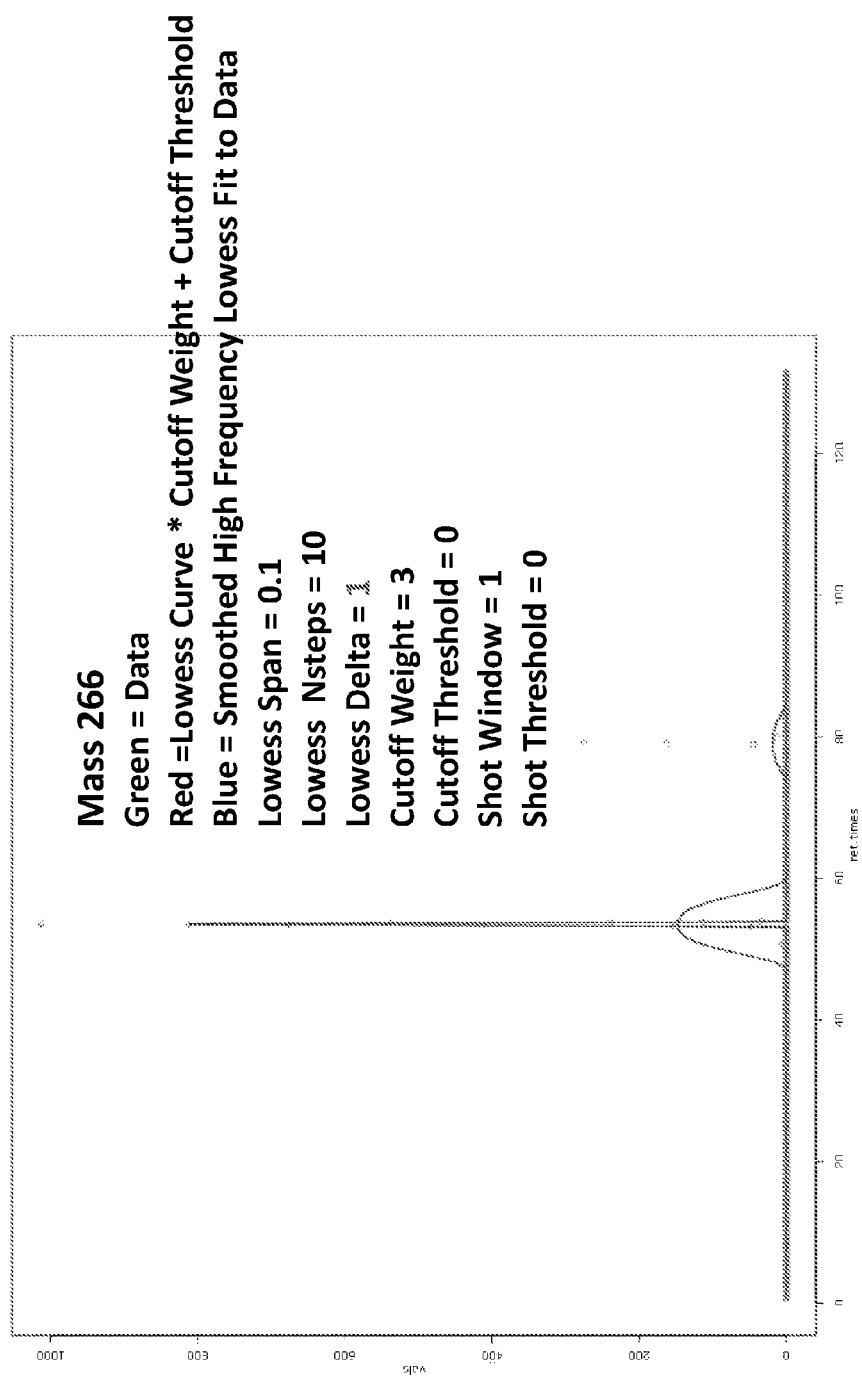
Figure 10:
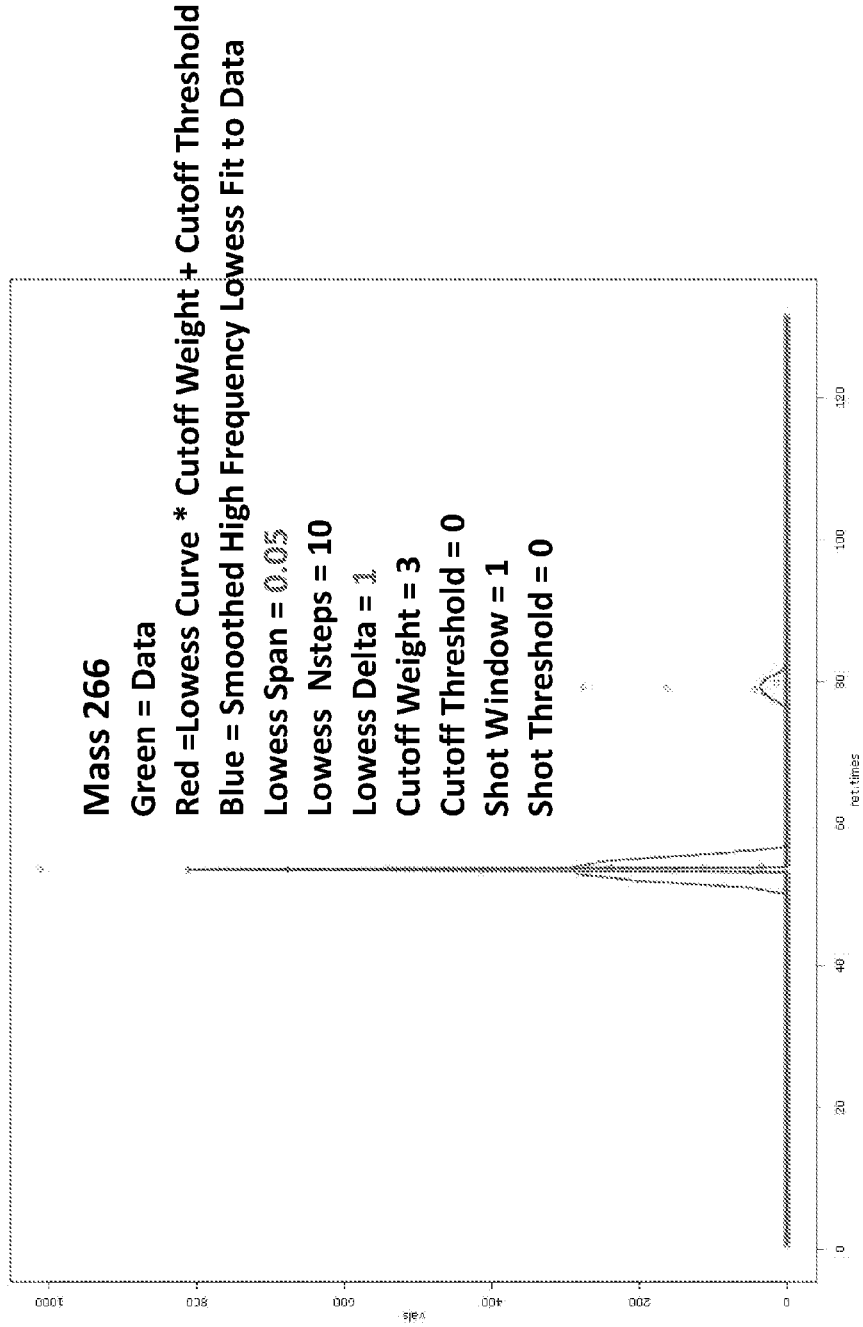

FIGS. 8 through 10 are all graphs of mass spectra data for Mass 266, where Lowess parameters are again changed in each figure in order to demonstrate the principles of operation of the embodiments.

Figure 11:
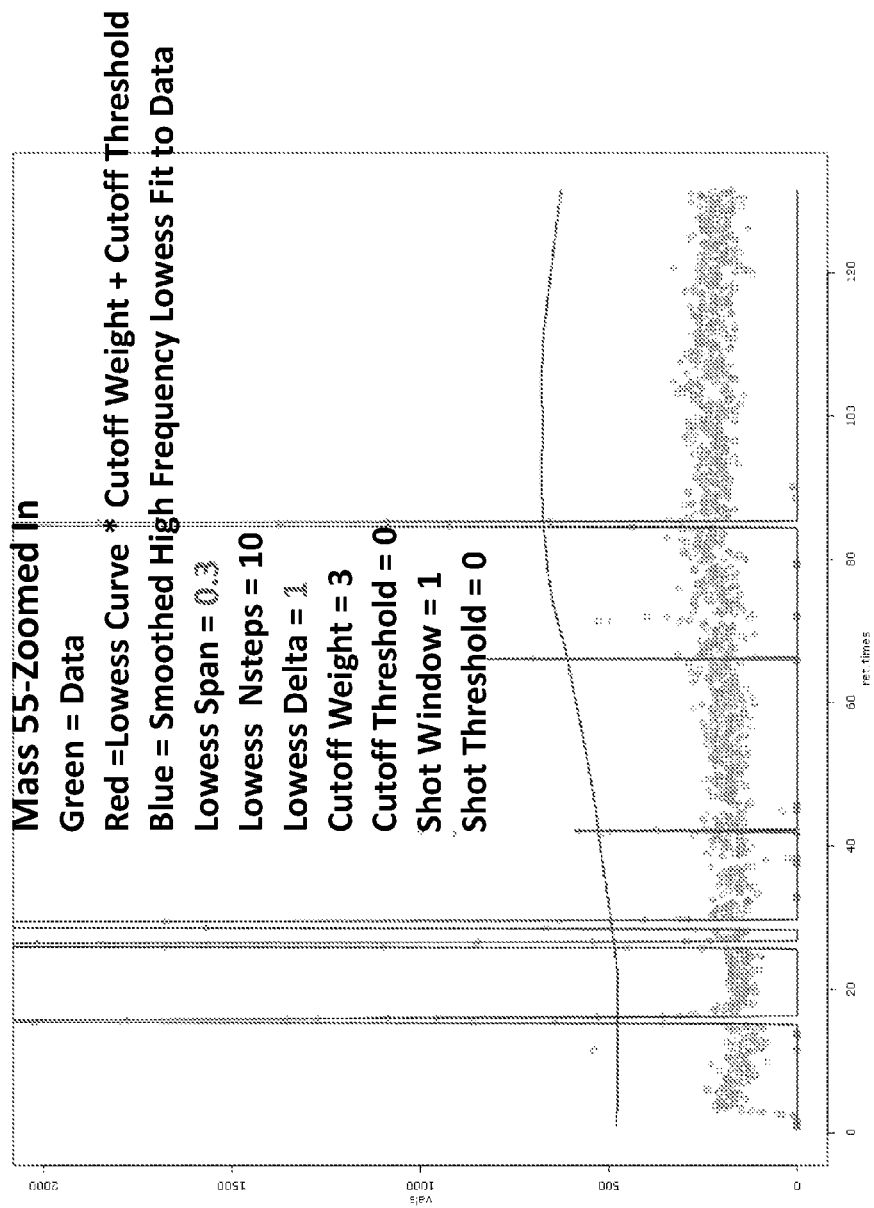
FIG. 11 is a graph of mass spectra data for Mass 55, but zoomed in to show more detail.
Figure 12:
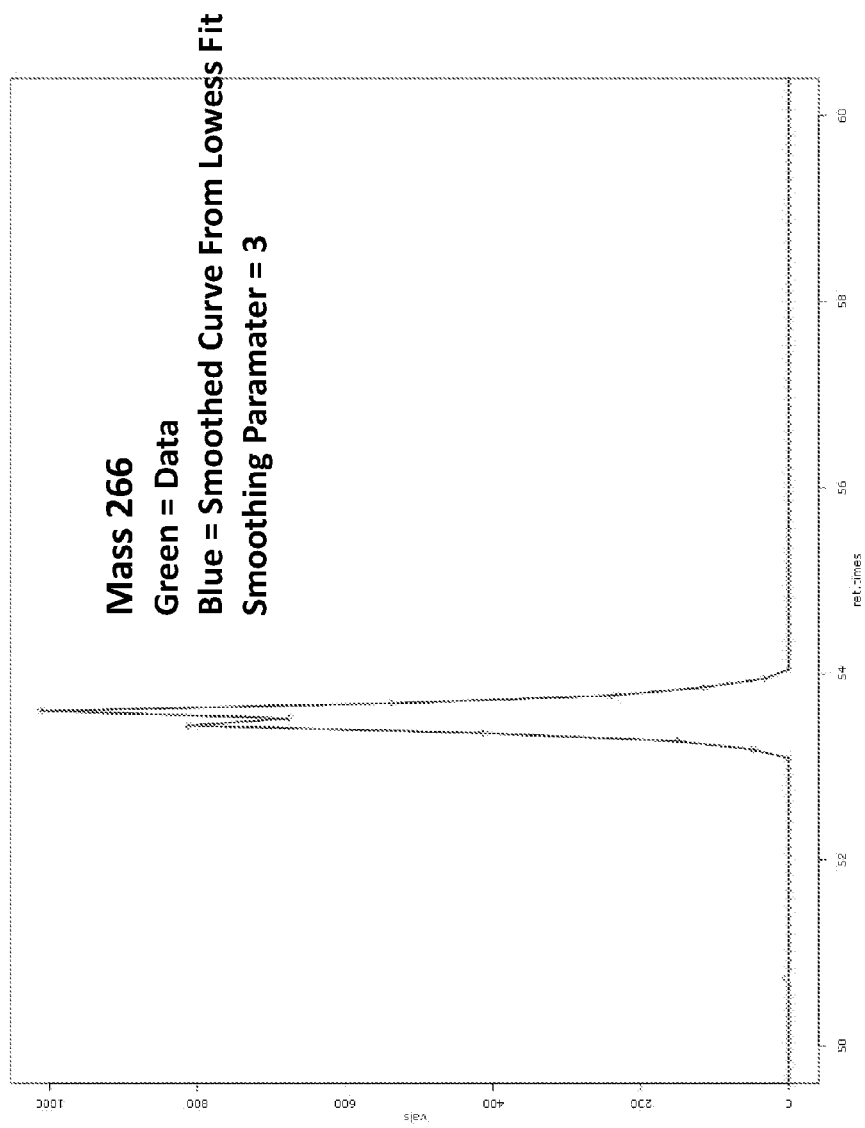
FIGS. 12 through 18 are graphs that illustrate Mass 266 with various smoothing parameters.
Figure 13:
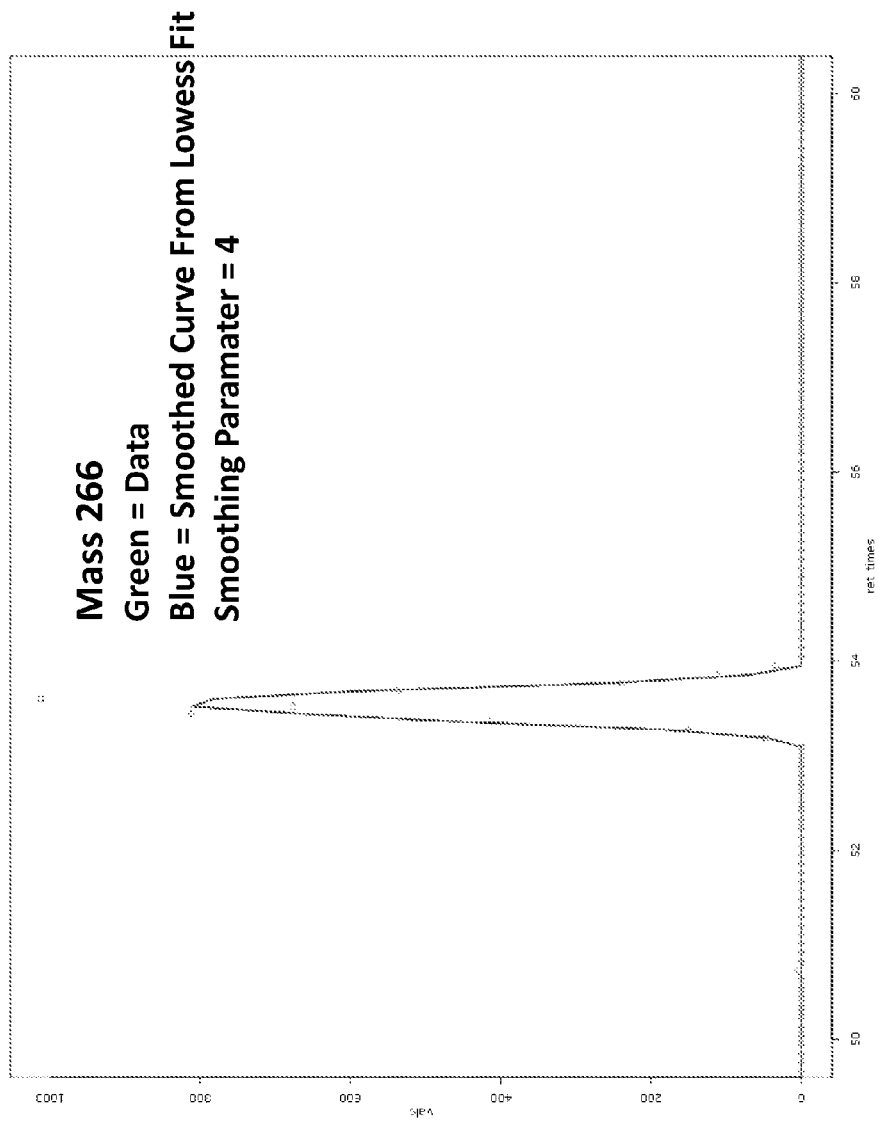
Figure 14:
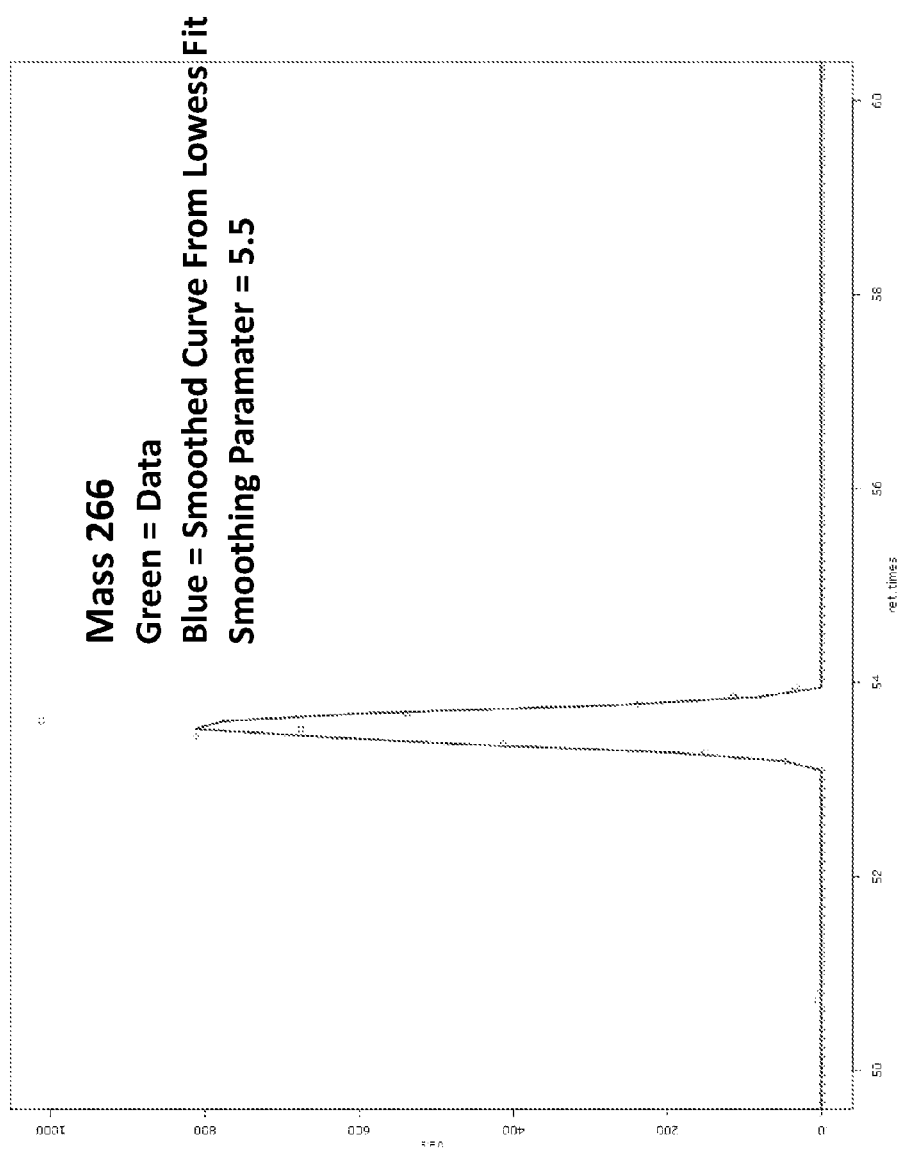
Figure 15:
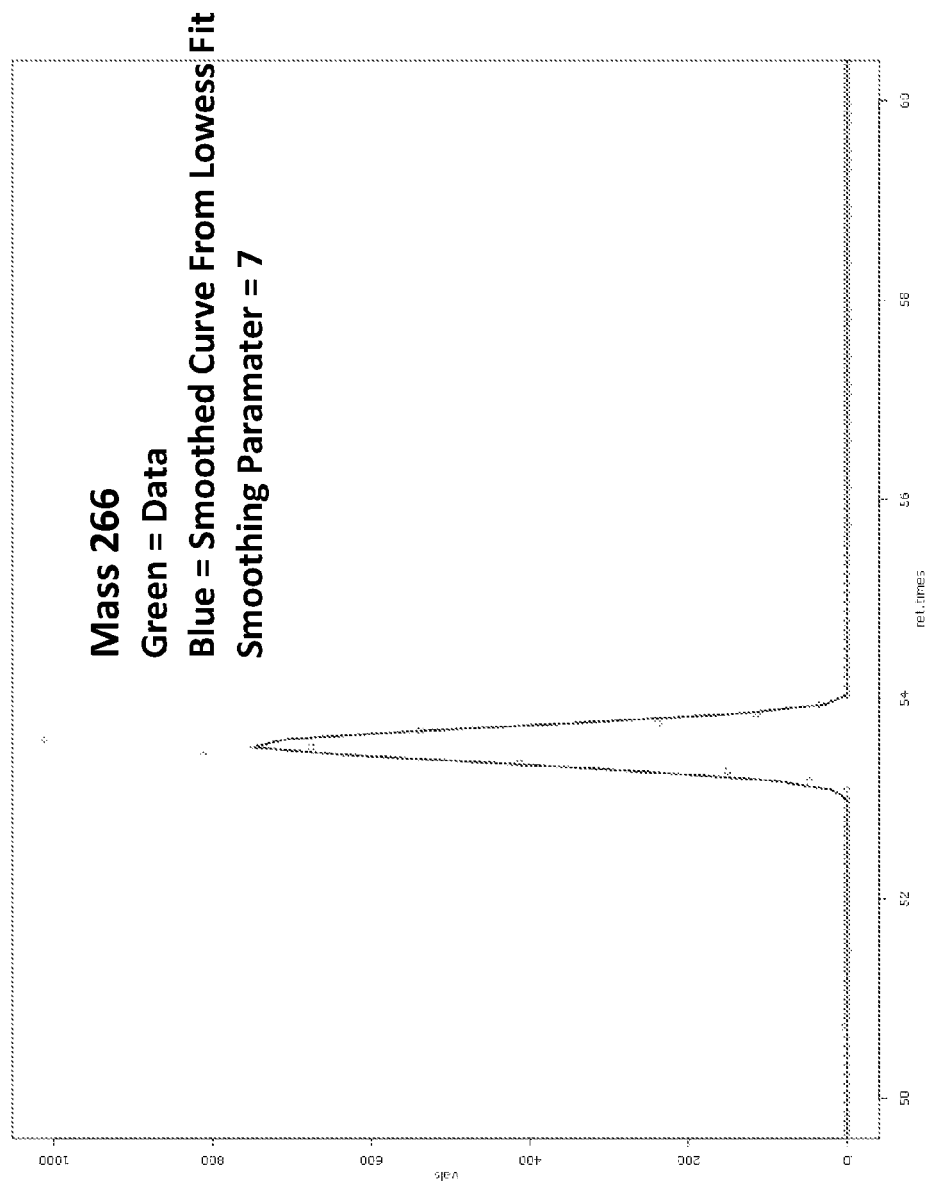
Figure 16:
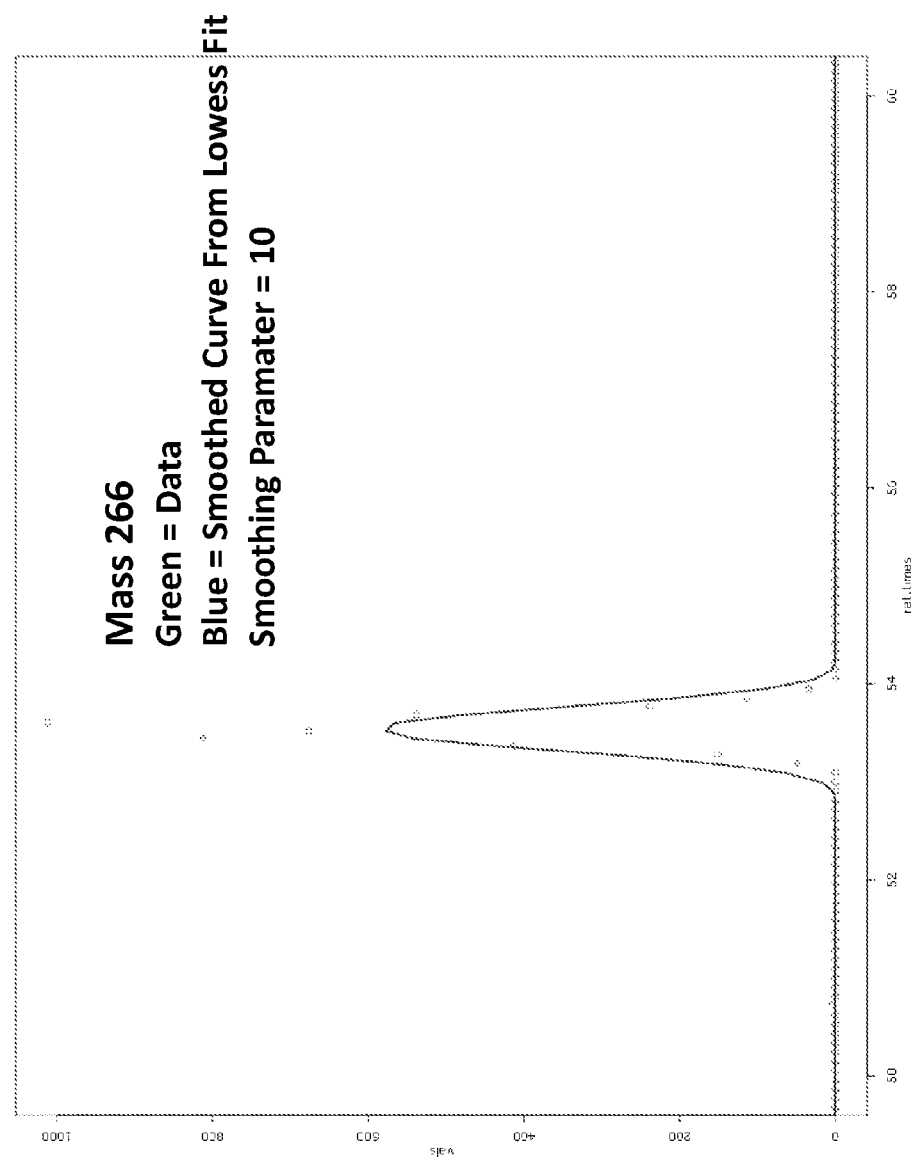
Figure 17:
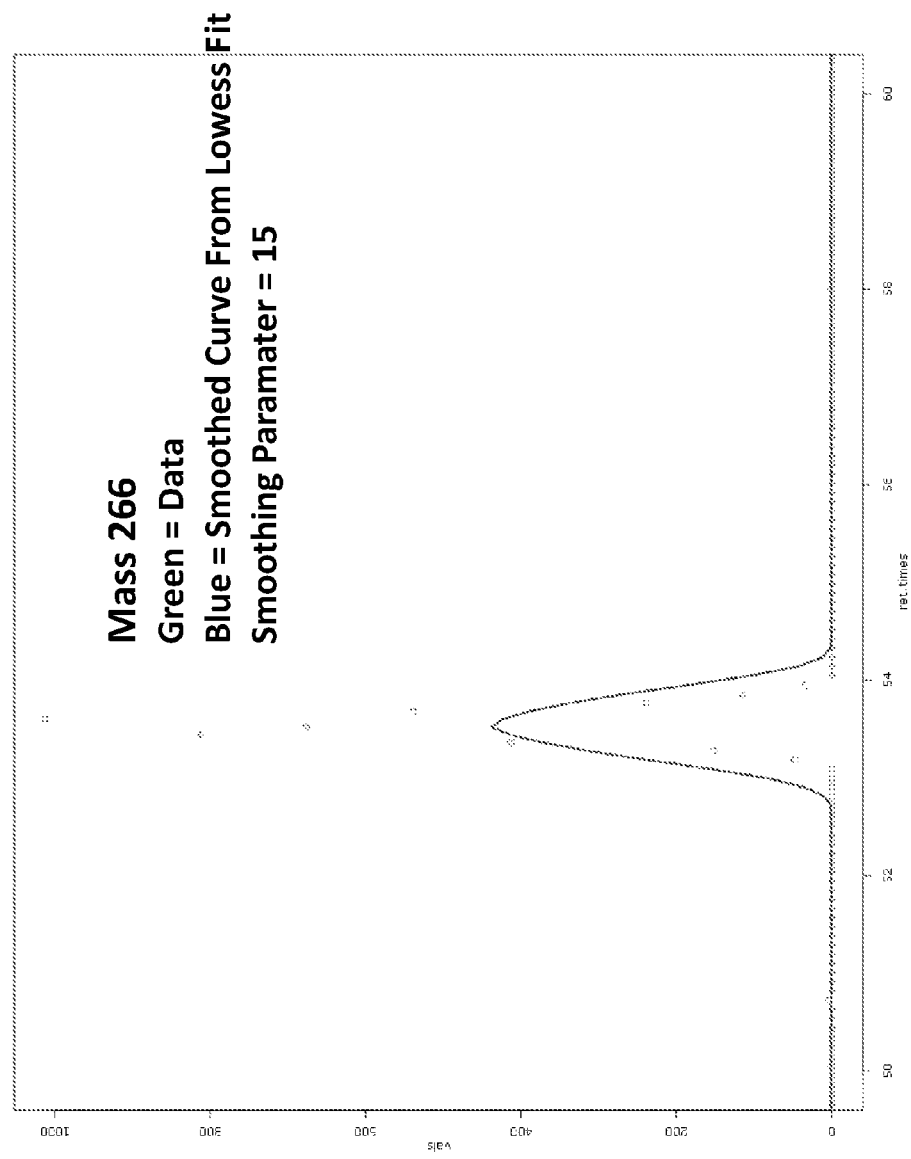
Figure 18:
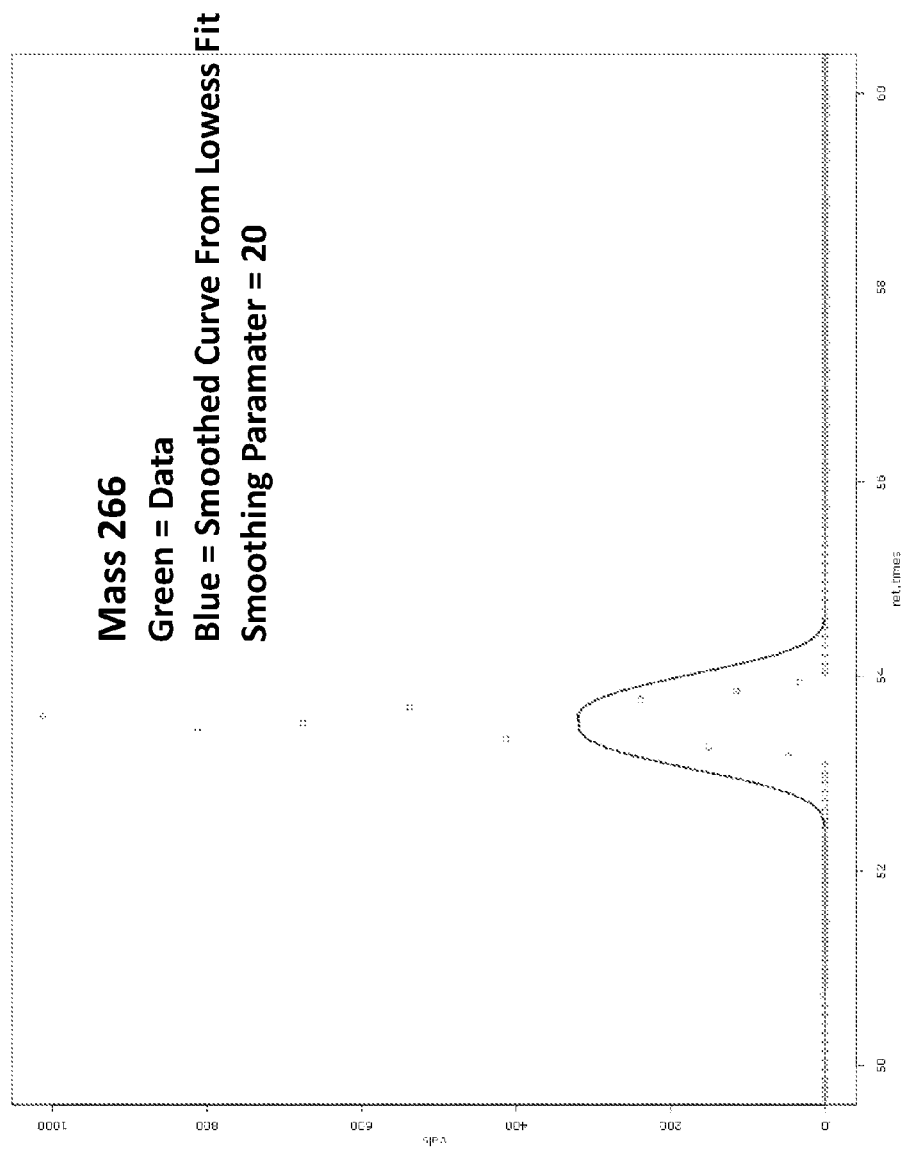
Figure 20:
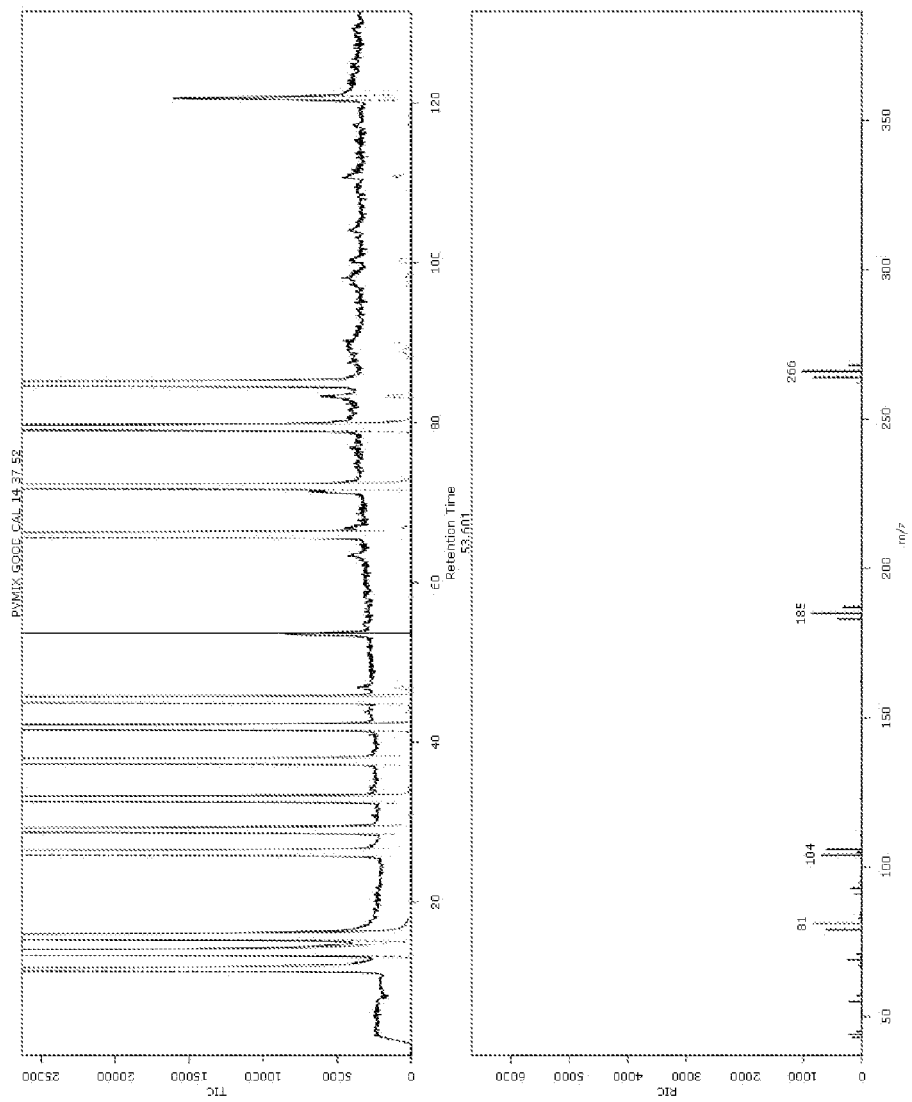
Figure 22:
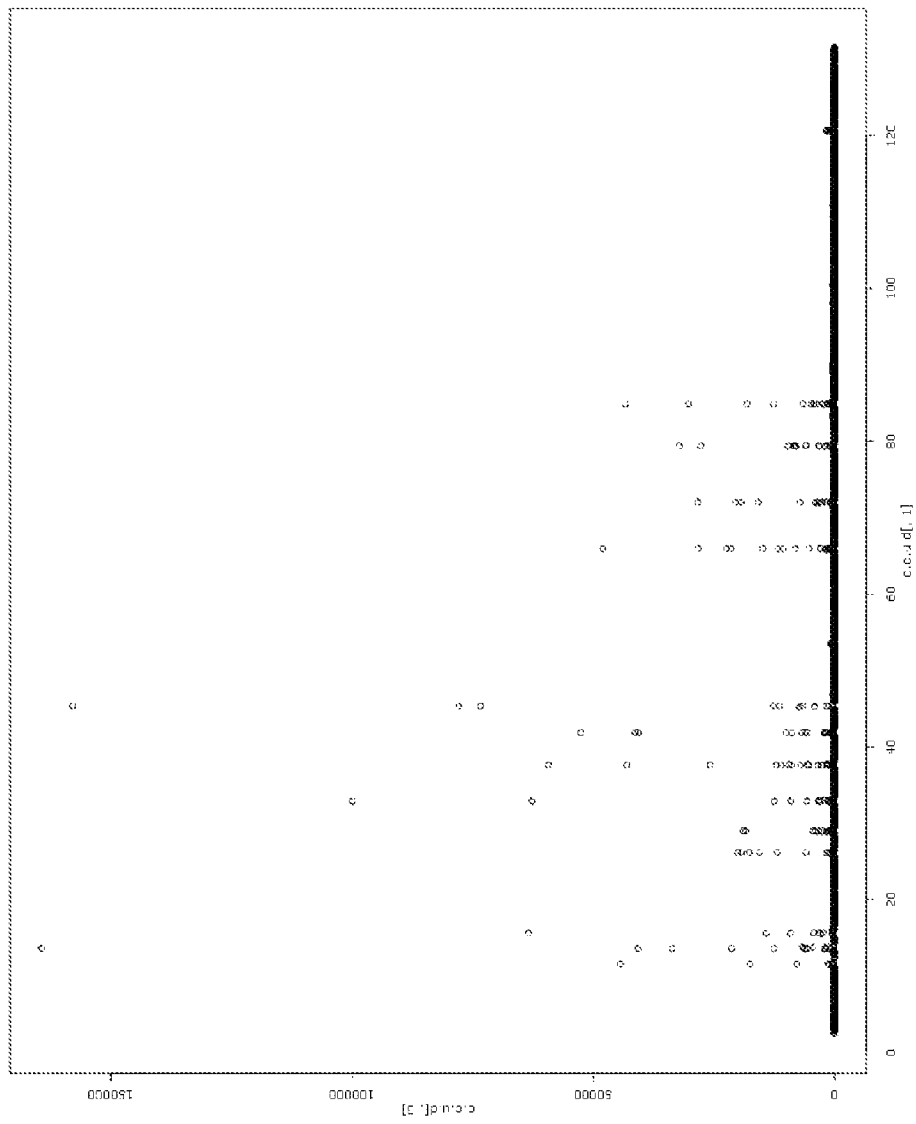
Figure 23:
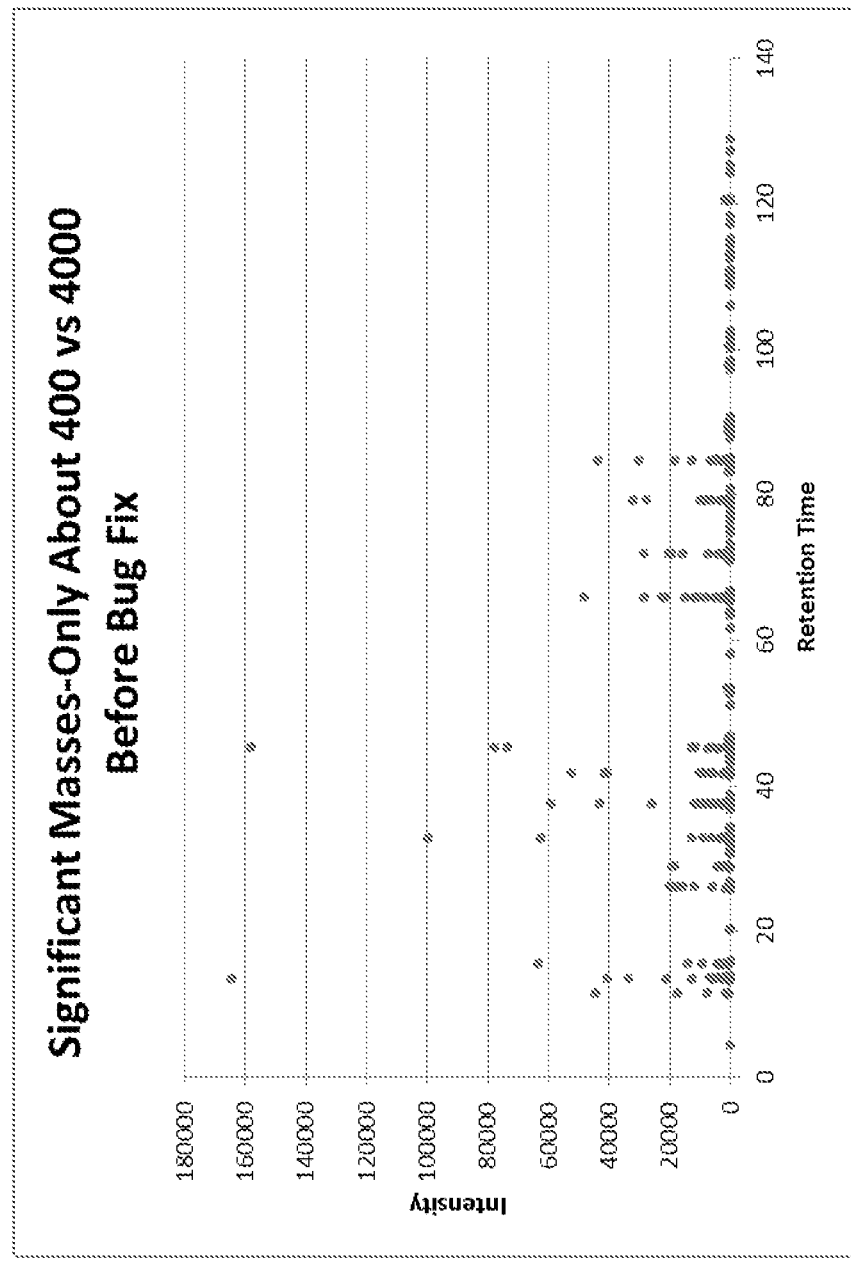
Figure 24:
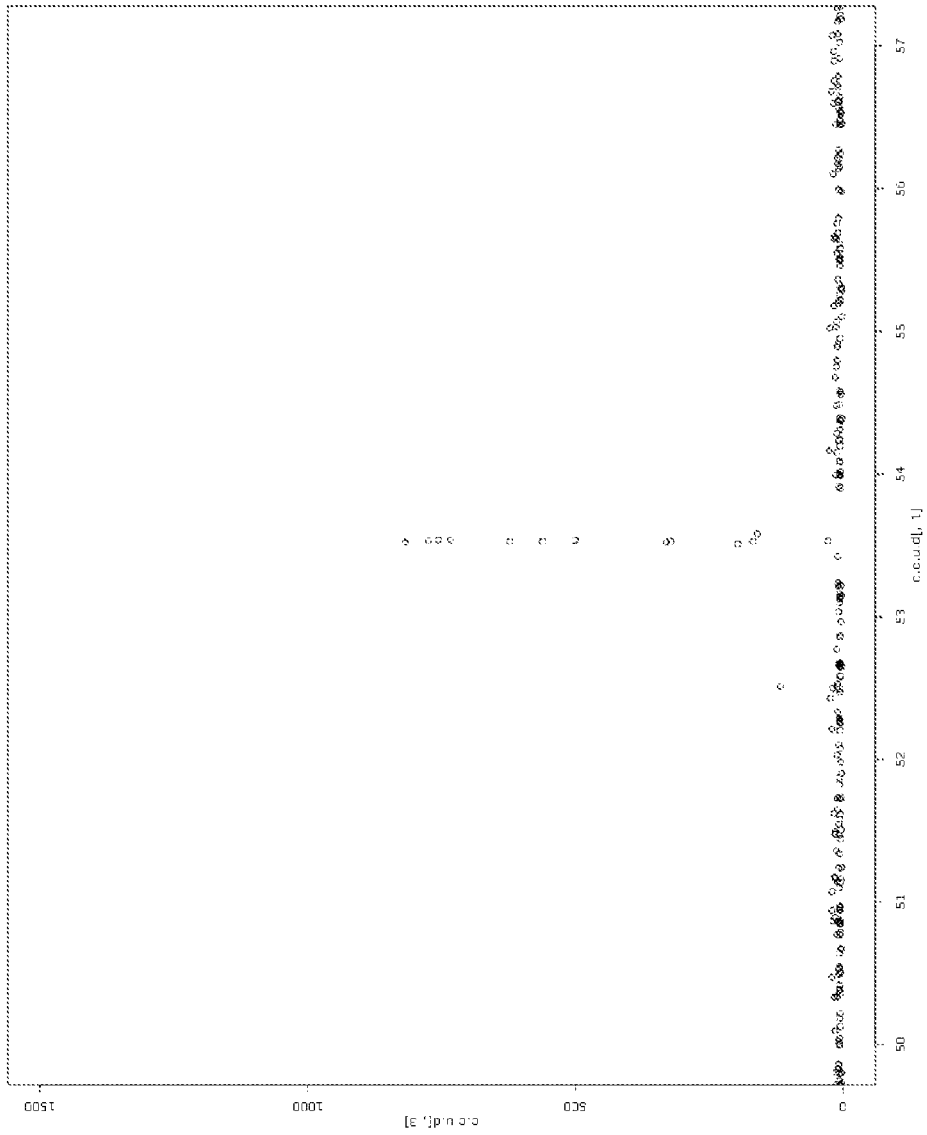
Figure 25:
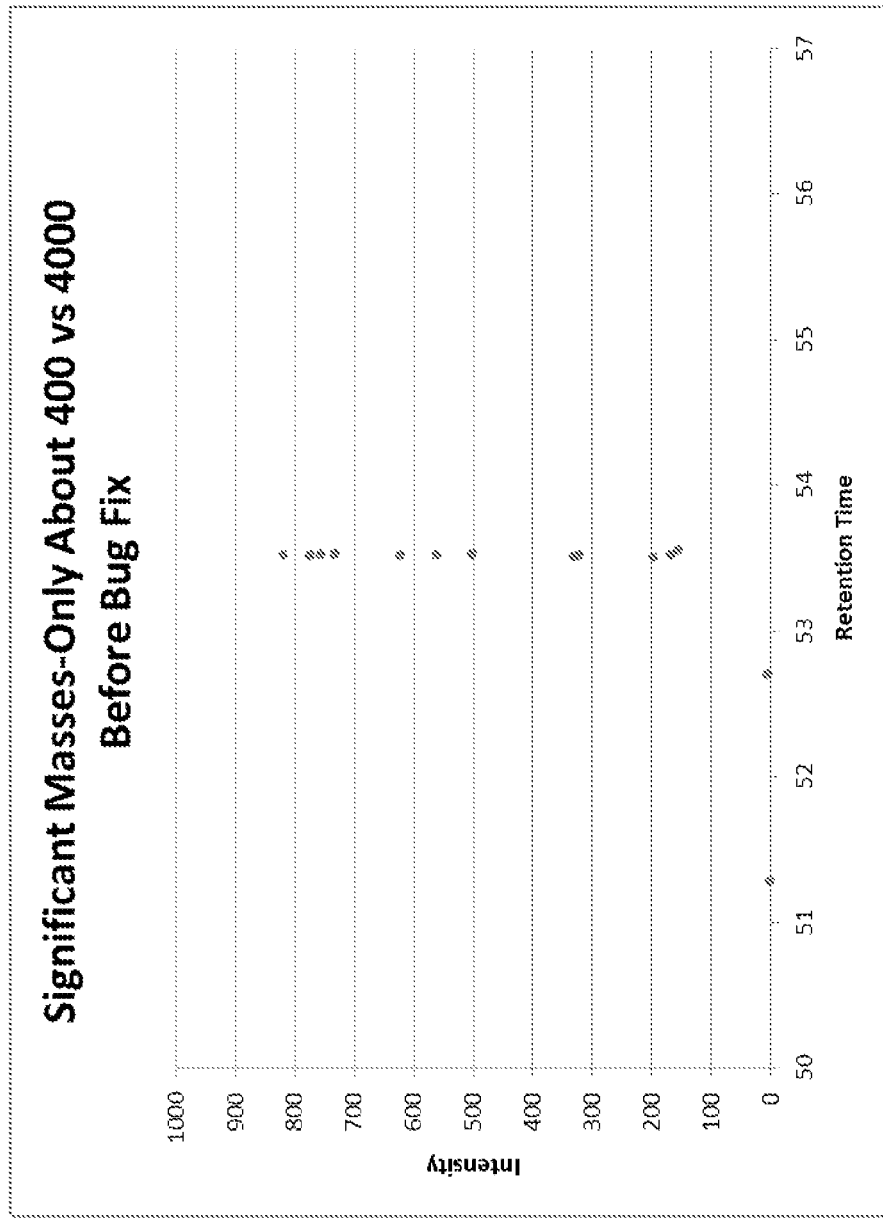
Figure 27:
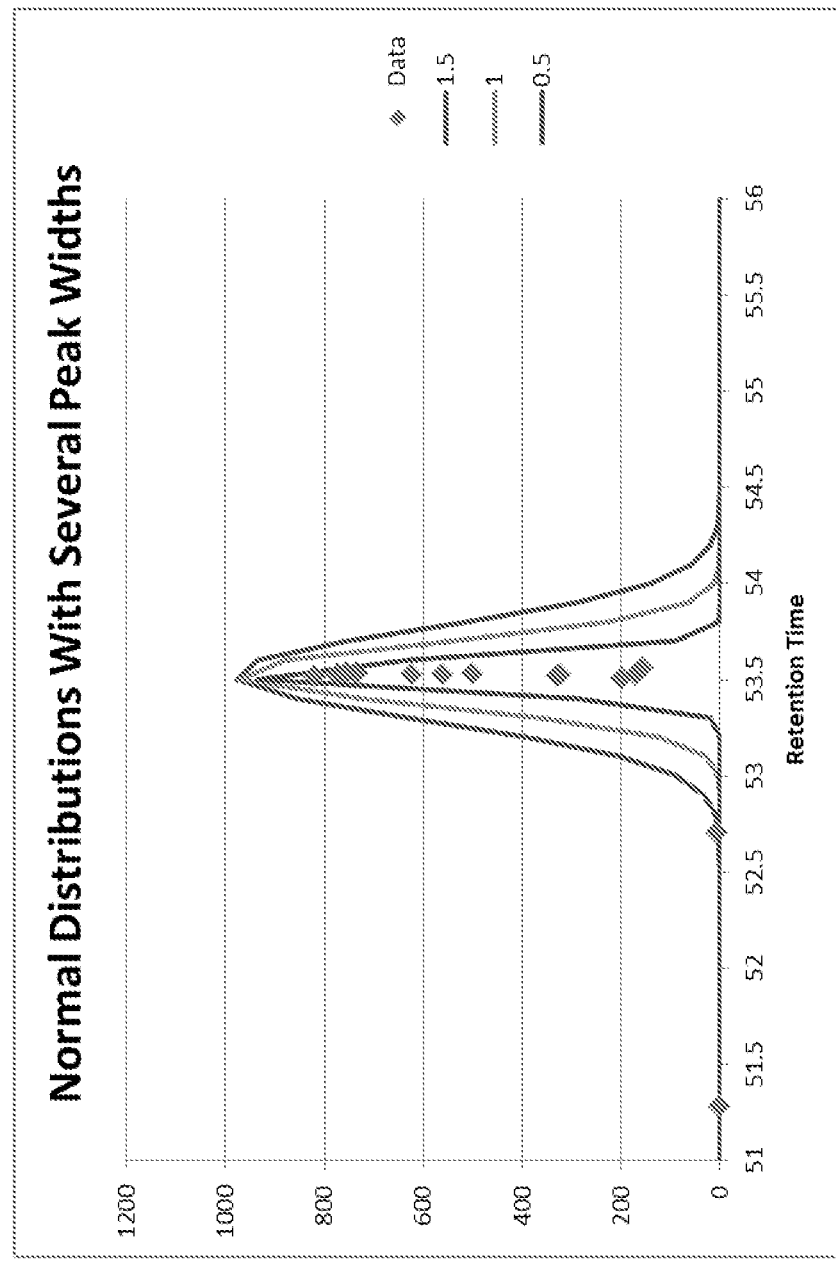
Figure 28:
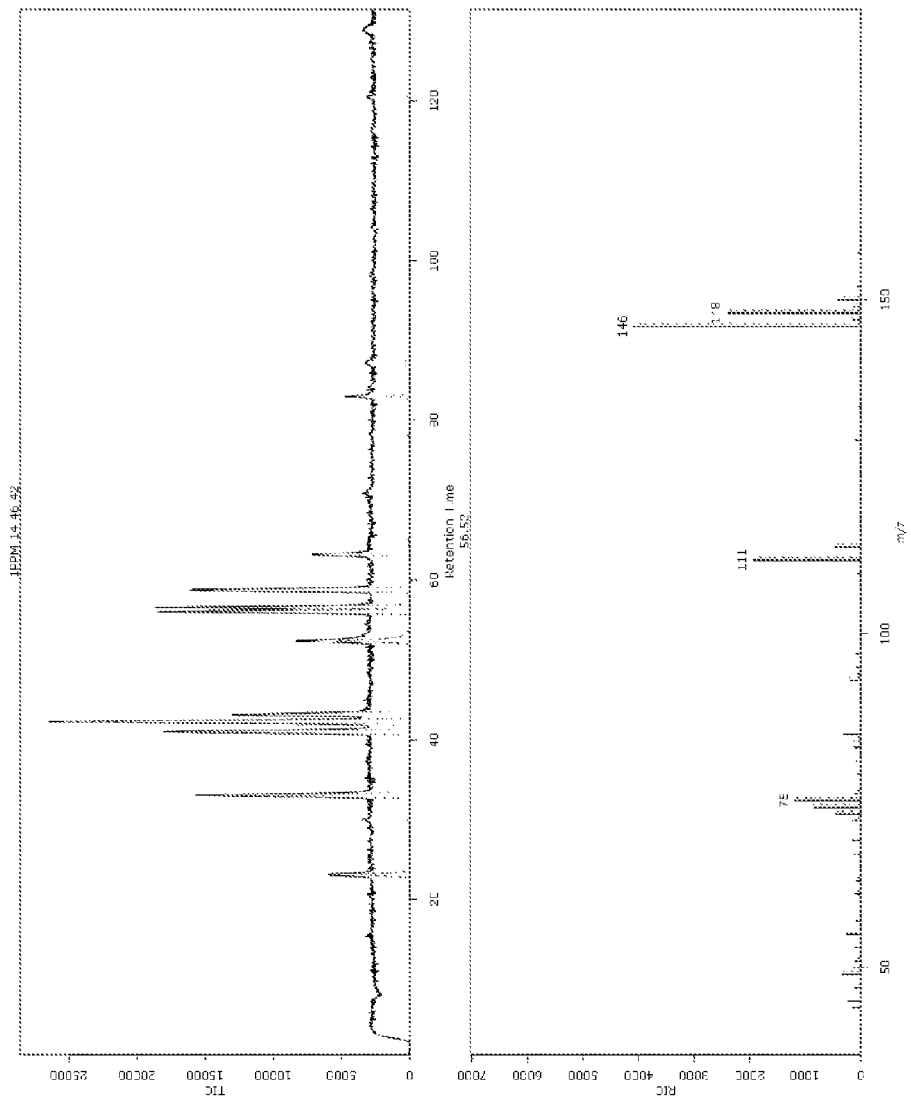
Figure 29:
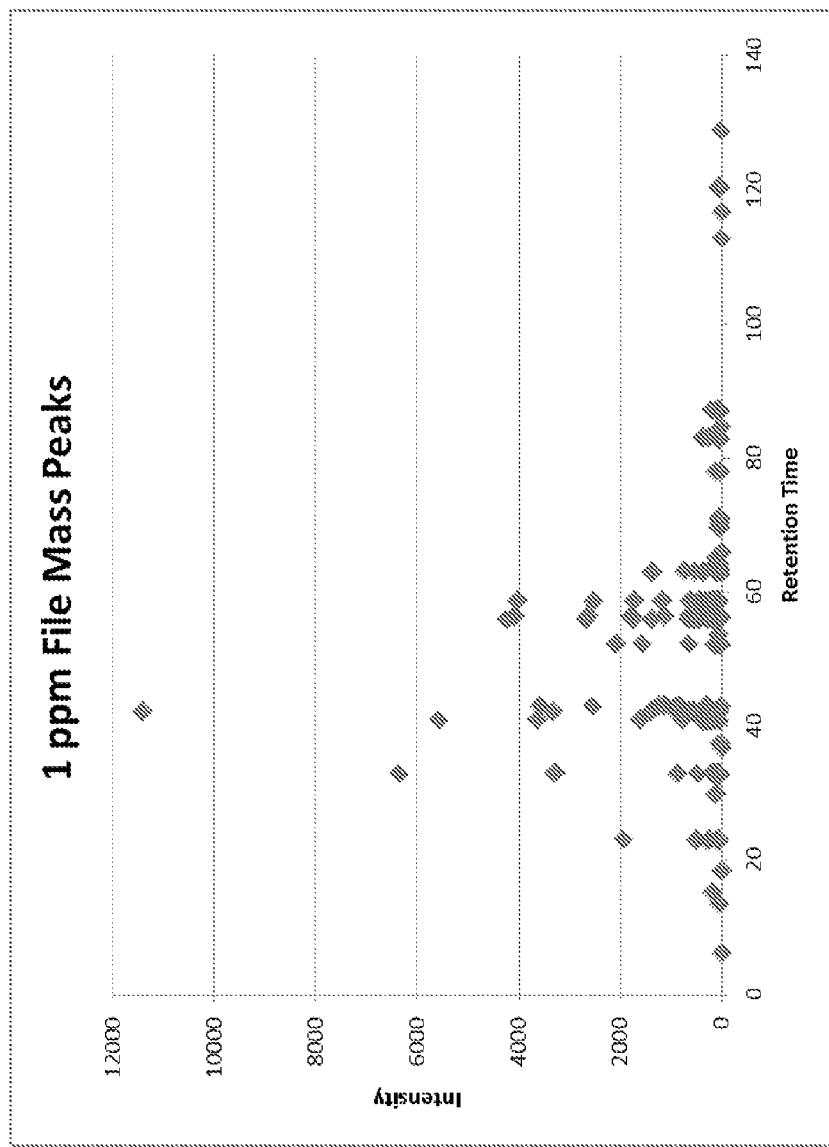
Figure 30:
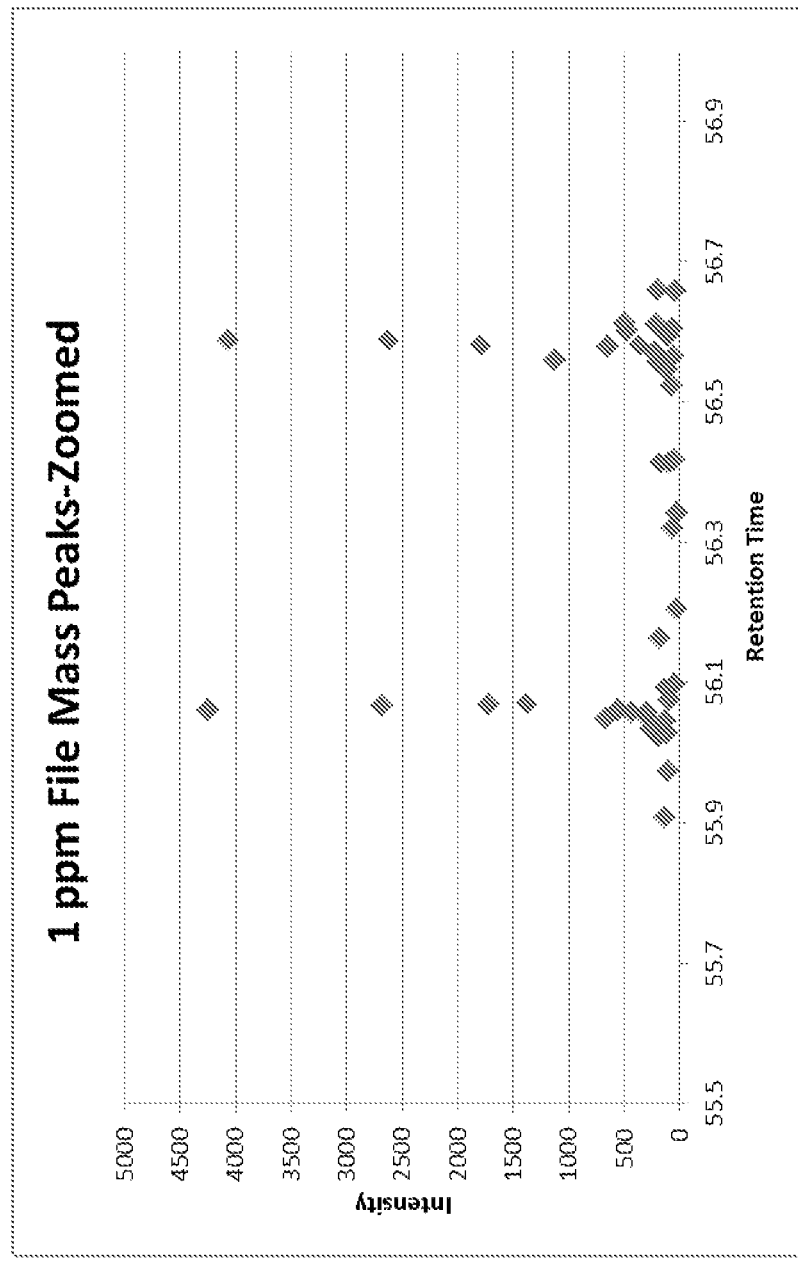
Figure 31:
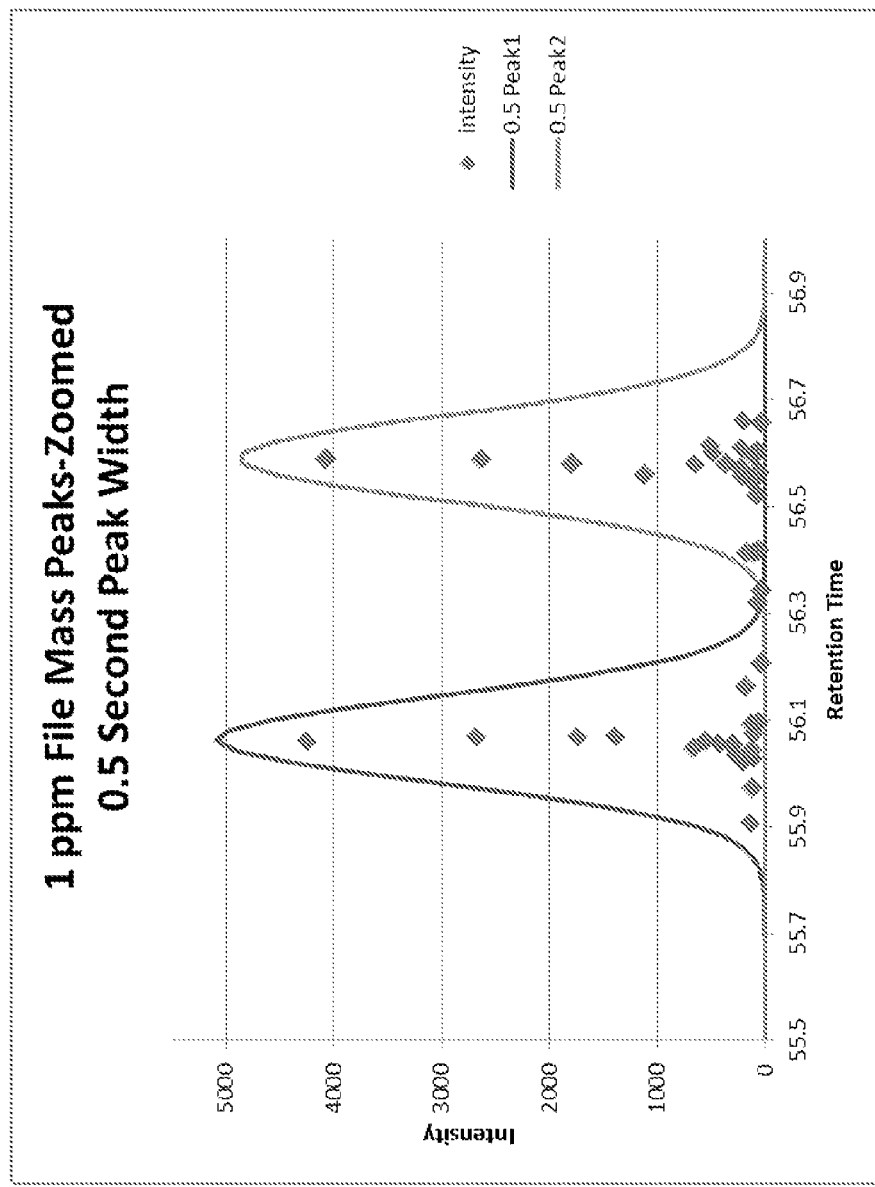
Figure 32:
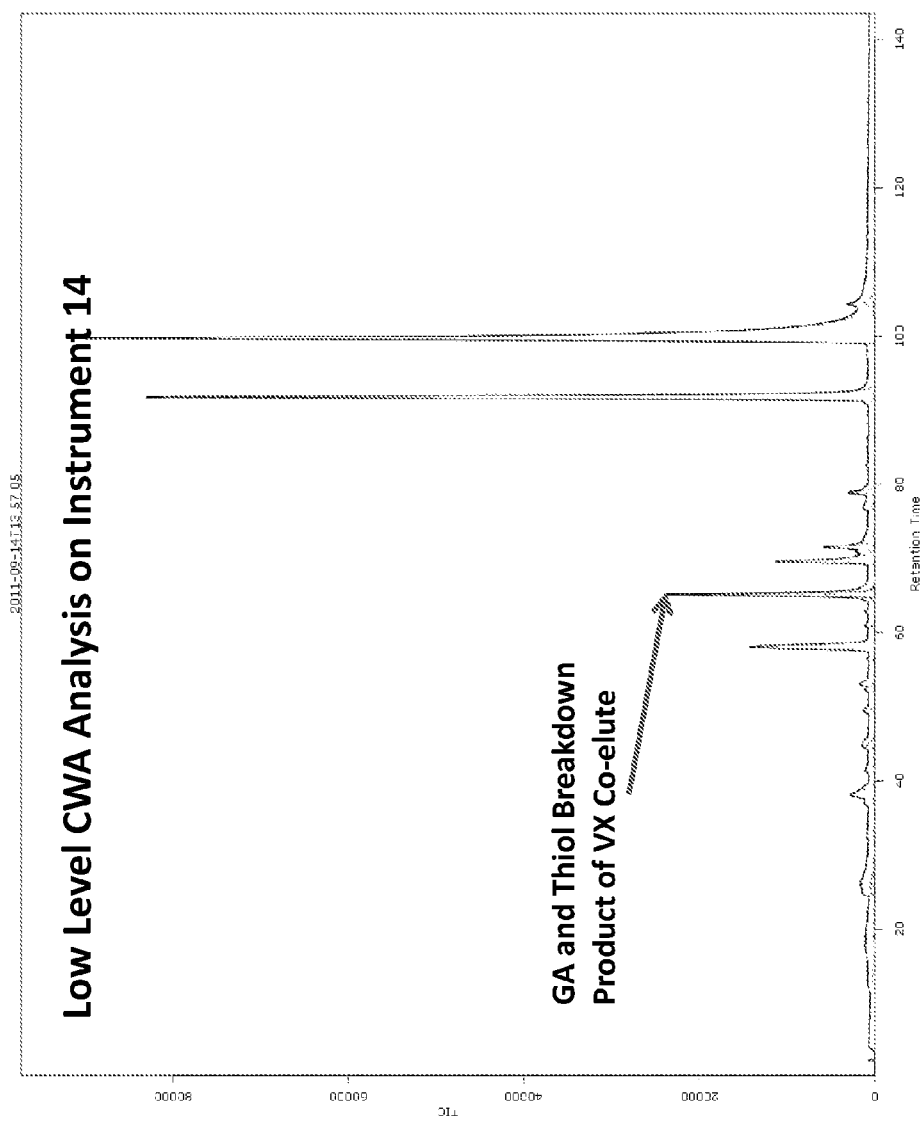
Figure 33:
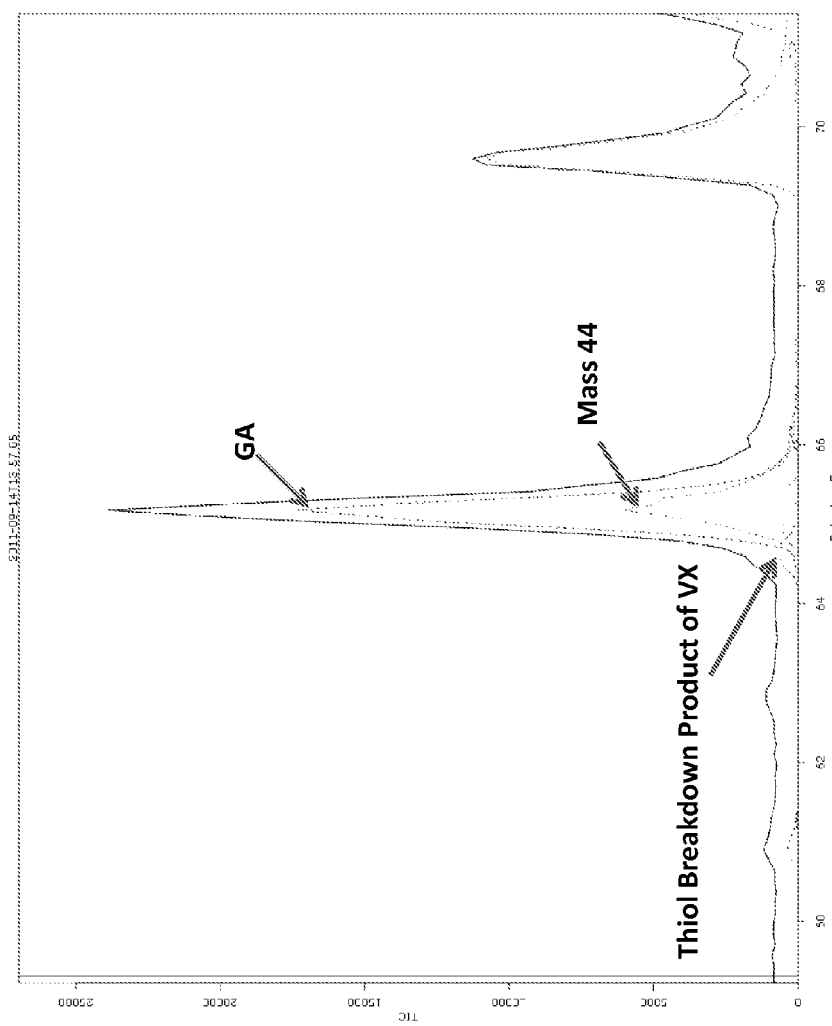
Figure 34:
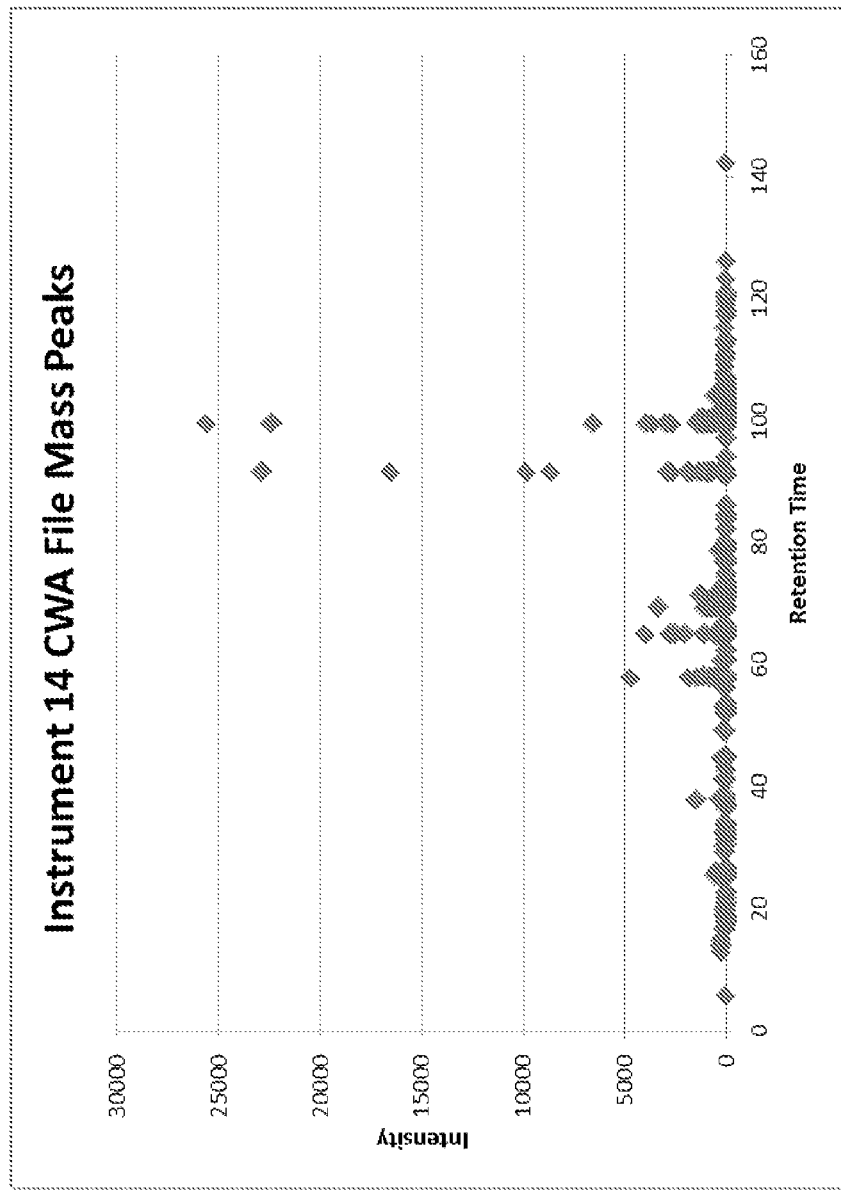
Figure 35:
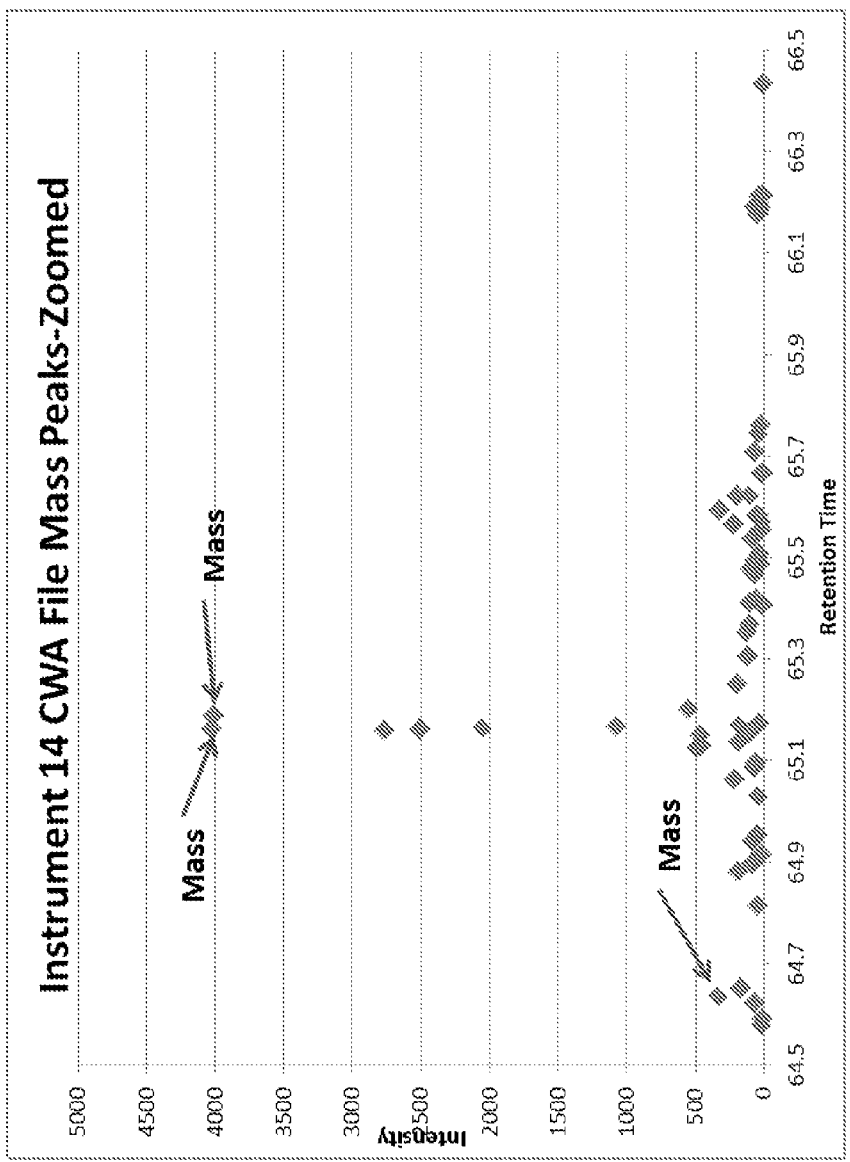
Figure 36:
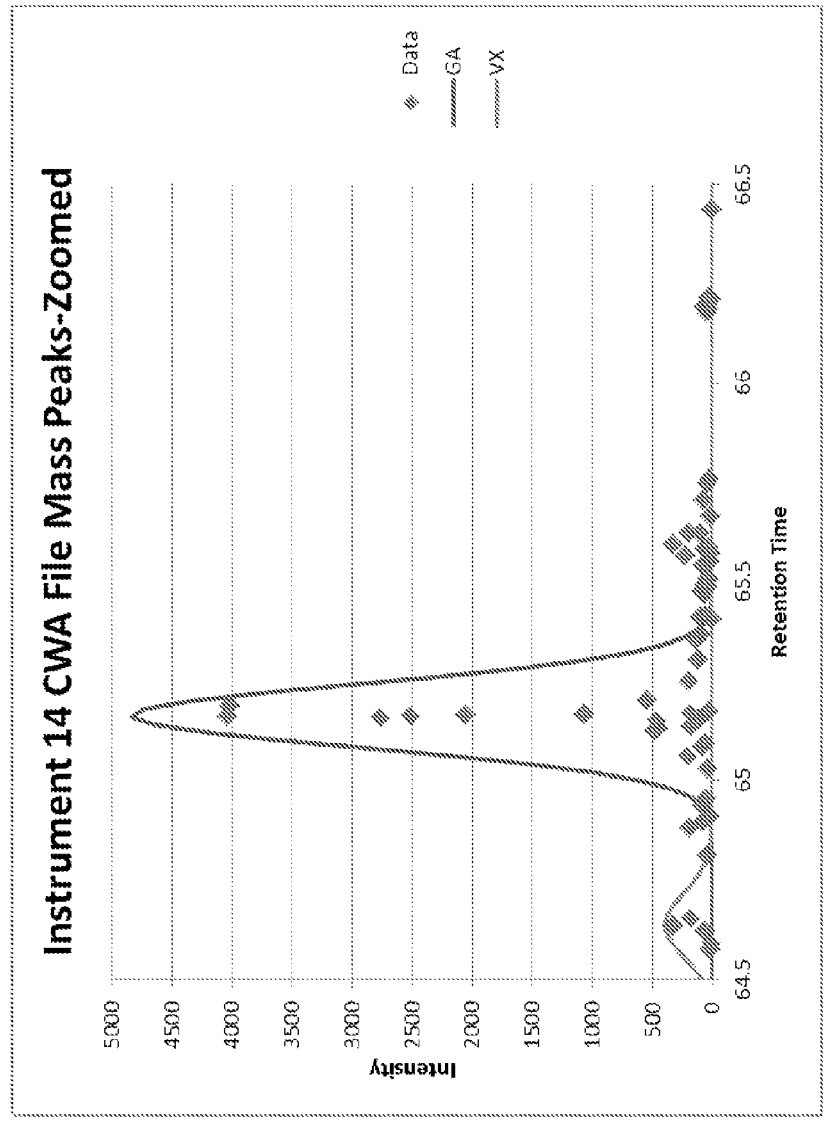
Figure 37:
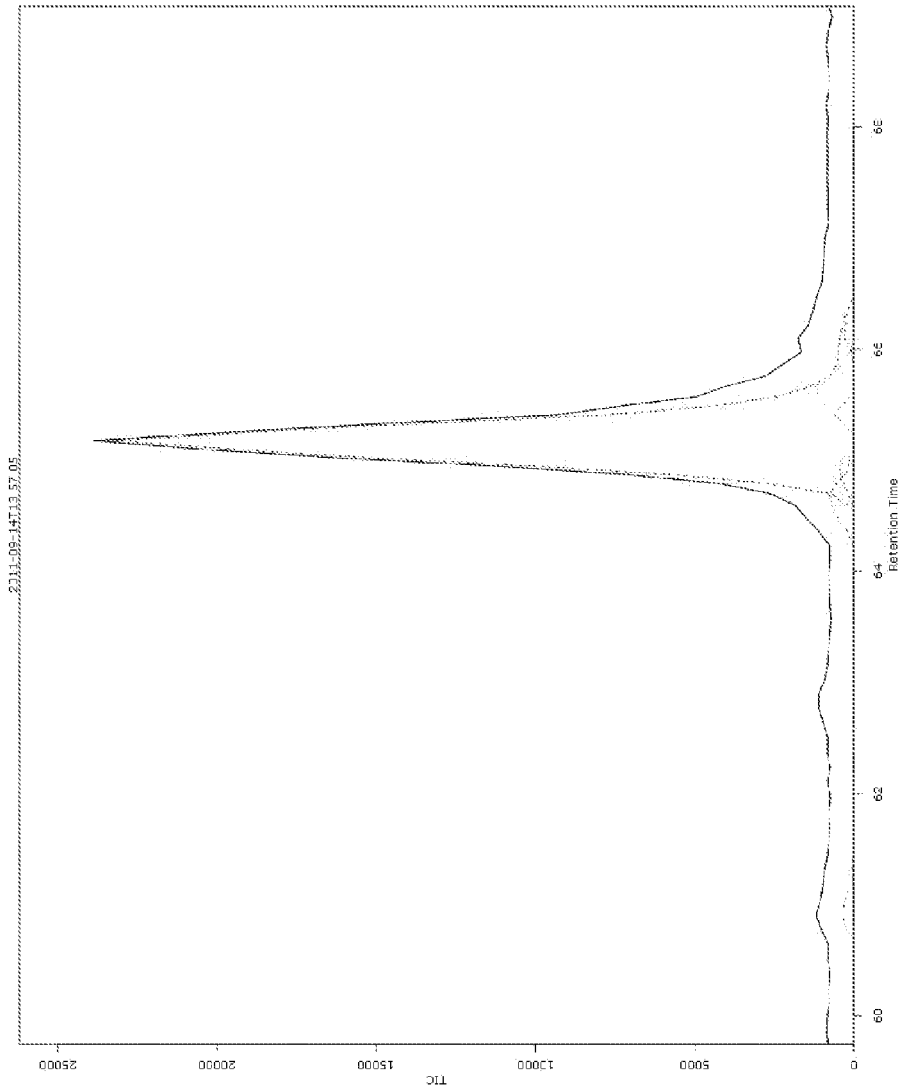
Figure 38:
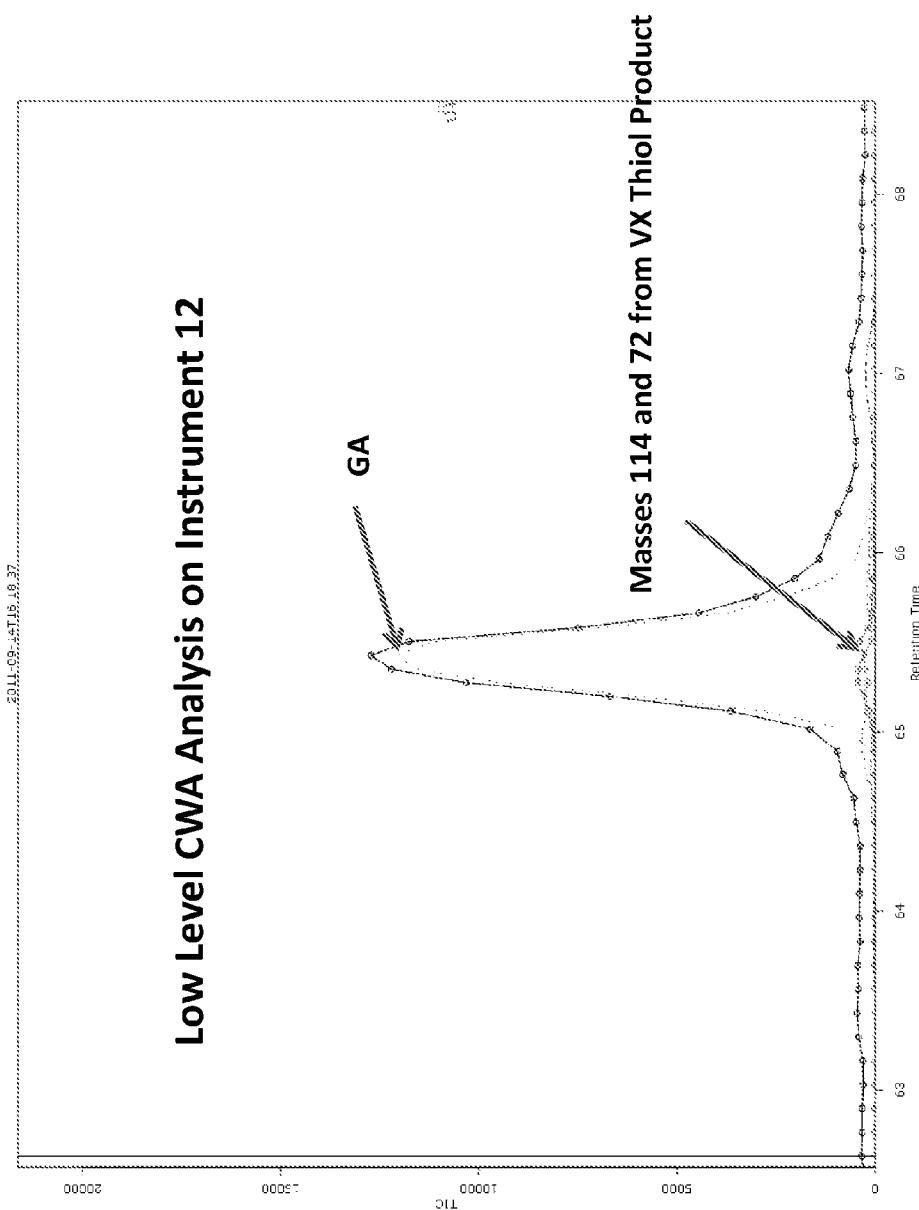

FIG. 11 is a graph of mass spectra data for Mass 55, but zoomed in to show more detail.

After background noise removal 10 is accomplished, the next step of the first embodiment is to perform deconvolution 12. Because a significant amount of noise has already been removed from the mass spectra data, the step of deconvolution 12 may now concentrate analysis on sharper signal peaks. Thus, while the Lowess algorithm in the second and third embodiments of background noise removal or a modified algorithm in the first embodiment of background noise removal may be used to remove background noise, the Lowess algorithm may also be used to identify signal peaks during deconvolution 12.

Deconvoluting co-eluting spectra is the next step of the present invention. The step of deconvolution 12 is performed in order to find and then group mass peaks that are close to each other temporally in order to create a good spectral representation of the peak that was present at particular points in time.

It has been determined that the deconvolution algorithm of the present invention may function better than the prior art when analyzing noisier data. This advantage of the present invention is made possible because background noise removal is performed before the step of deconvolution 12.

For example, when operating a GC\MS device that is not in a laboratory, the mass spectra data may have much more noise which can obscure real data. Thus, the present invention is particularly well-suited for analyzing data that is obtained from an inherently noisy source, such as a portable GC\MS device.

In general, the step of deconvolution 12 includes the steps of smoothing all of the peaks using an appropriate smoothing filter, finding each peak, and then grouping the peaks.

Therefore, with the background noise now removed, it may be assumed that what is remaining is actual mass spectra data with less noise. For all the scans of each mass (RIC), an appropriate filter may be applied for the purpose of smoothing the peaks. Smoothing filters that function as desired include the Lowess and the Hanning filters, but the present invention should not be considered to be limited to these smoothing filters.

The present invention may apply a smoothing filter over a smaller time span than when performing background noise removal 10. The span may be defined as a Smoothing Parameter (typically using a value of around 7) divided by the total number of scans (typically between 1000 and 2000). Applying the span as defined may function as a smoothing filter.

Using the three highest points of each peak of a mass, a parabola is fit to the data points in order to find the intensity of the peak and the precise time of the maximum point of the peak. It should be understood that none of the three data points may end up as the maximum point of the peak. The resulting parabola gives an intensity, time, and mass for each peak in the mass spectra data.

After the peaks are now found, the next step is to group the peaks into compounds. In general, the next step is to group peaks by comparing retention times and heights of the peaks.

A specific implementation of grouping peaks is to choose the peak with the largest intensity because this will be the "main" ion which may be assigned an intensity of 100 because it is a simple value to work with. The next step is to draw a normal distribution around the peak of the main ion which has a mean equal to the exact time, a height equal to 1.2 times the exact intensity, and a standard deviation equal to the peak width (typically 1.5) times 160. These values may be adjusted as necessary and should not be considered as limiting. However, these values are selected based on their ability to achieve the desired results.

All other peaks whose intensity and retention time place them within the normal distribution of the main ion are then grouped with the main ion. When the other ions near the main ion are being evaluated to determine if they fall within the normal distribution of the main ion, the intensity of the other ions may be converted to be a percentage of the main ion. All other ions having an intensity above 25% may be designated as "necessary" ions for the compound, while all others may be designated as "unnecessary" ions. The selection of an intensity of 25% as making the ions necessary may be adjusted as necessary to achieve the desired results.

All other ions that are added to the compound of the main ion are then given a confidence value of 20%. This process is repeated with the next highest remaining peak now being designated as the main ion until all peaks have been grouped and no more peaks remain.

After all peaks are assigned to a group, it may be determined that some peaks were assigned to the wrong group. For example, some peaks may need to be reassigned from one group to another if they fall within two or more normal distributions of different ions. For example, a first ion may be grouped with a first peak because it falls within the normal distribution of the first peak. When a second peak is designated as the main ion, it may be found that the first ion is also within the normal distribution of the second peak. In that case, the first ion will be grouped with the peak that has the closest retention time to its own. This means that the first ion may be grouped with the second peak if it meets the criteria described above.

It may also be the case that the first ion also falls within the normal distribution of yet another peak. The first ion will be grouped with the peak having the closest retention time to its own.

Each group potentially represents the retention time and mass spectra of a compound that was in the data, which are referred to as the "Unknowns". The retention time is the exact time of the highest peak of the group. The mass spectra is the combination of the mass and exact intensity of all the peaks in the group. In cases where two or more peaks represent the same mass, the peak with the highest intensity is used to identify the mass.

FIGS. 12 through 18 are graphs that illustrate Mass 266, where each has a different smoothing parameter. The table shown in FIG. 19 shows the smoothing parameter that was selected and the corresponding calculated retention time for Mass 266. The smoothing parameter may have approximately the same number as the number of scans in a typical chromatographic peak. The calculated retention time or retention index is not a strong function of the smoothing parameter; however it is best that it not be so low that peaks that should be single are split, or so high that peaks that should be split come out as single.

FIGS. 20 through 38 are graphs that demonstrate various results of deconvolution applying the first embodiment of the present invention.

FIG. 1 shows that after compounds have been grouped through deconvolution 12, the next step is to determine a correlation value 14 for each of the compounds that was grouped together during the process of deconvolution 12.

For example, a user may provide a target list of compounds that may be in the spectroscopic data that was delivered for analysis. There may be a good chance that a particular compound on the target list may be found in the spectroscopic data. In other words, a particular unknown compound and a compound on the target list may have a high correlation value. A correlation value may be determined for each of the unknown compounds as they relate to each of the compounds in the target list. It should be understood that some unknown compounds in the spectroscopic data may not realistically be a particular compound on the target list, and therefore no correlation value needs to be calculated.

The step of correlation 14 is therefore calculating match statistics or a match factor for each unknown compound against each compound provided in the target list. These statistics may enable the system to determine if a target compound is present in the mass spectra data.

A first match statistic is spectral purity. Spectral purity is calculated using a "forward mass correlation". Peaks in an unknown compound beyond those listed in a target compound from the target list will lead to a lower value of spectral purity. The mass correlation may be calculated using a "reverse mass correlation". Extra peaks in the unknown compound do not lower the value. The retention correlation is calculated as $e^{(((exact\ retention\ time\ of\ unknown-retention\ time\ of\ target\ compound)/(max\ retention\ time\ of\ target\ compound-min\ retention\ time\ of\ target\ compound))^2)}$. A correlation value is also calculated as the combination of both the mass correlation and the retention time correlation. A supplied alpha value (typically 0.5, but it must be between 0 and 1) may determine how they are combined using the equation:

$$(alpha\ mass\ correlation) + ((1-alpha) * retention\ time\ correlation).$$

It should be understood that there are a number of scenarios in which a correlation value may not be calculated for a given "unknown compound-target compound combination". These scenarios include but may be limited to 1) if the user has specified that the retention time for a compound must be within the retention min-max window, then any unknown with a retention time correlation outside of the window will be skipped, 2) if the user has specified that all of the necessary (including the main ion) must be present in the unknown, then any unknown that is missing those ions will be skipped, 3) if the user has specified that all necessary ions must have an intensity within a certain ratio window, then any unknown that does not have all necessary ions in the window will be skipped, and 4) if the user supplied minimum correlation value is greater than the calculated correlation value then it will be skipped.

It is noted that one method of calculating spectral purity is as follows:

$$Spectral\ Purity = forwardMassCorr = (XS*XS)/(X*S)$$

Match Factor maybe calculated as:

$$Match\ Factor = reverseMassCorr = (XS*XS)/(XO*S)$$

where
XS=SumOf(Sqrt(unknownIntensity*knownIntensity))
X=SumOf(unknownIntensity)
S=SumOf(knownIntensity)
XO=SumOf(unknownIntensity that had a knownIntensity above zero at the same mass)

Once the correlation values have been calculated for the unknown compounds in the spectroscopic data, the next step in the first embodiment shown in FIG. 1 is to perform sorting 16 of the compounds.

It is important that as compounds (unknowns and potentially target compounds) are removed from the spectroscopic data that they be removed in the correct order. This is important because if it is suspected that a small compound is present underneath a larger one, then removing the larger compound first would leave none of the smaller compound in the spectroscopic data, and the compound would therefore not be identified.

Therefore, the first embodiment shown in FIG. 1 includes the following embodiment for sorting 16 the compounds. The first step is to sort all of the unknown compound and target compound combinations by the calculated correlation values. If the spectral purity of a particular unknown compound and target compound combination is below the purity threshold (typically 50) and the target compound does not have a higher correlation value to a different unknown compound, then the mass spectra data for the target compound supplied with a target list is next on a list of compounds that are considered to be sorted. All of the correlation values are evaluated, adding the target compound spectra of any compound that meets the above criteria. All of the unknown compounds are added to the sorted list after any target compounds are added. The unknown compounds are added in order of height from biggest to smallest.

The next step of the first embodiment shown in FIG. 1 may be characterized as removal 18 of the compounds one by one in the order that they were sorted in the sorting step 16. Given an arbitrary spectra, a retention time, and retention window, as much of each ion as possible may be removed from the spectroscopic data that has had the background noise removed. The spectroscopic data that is removed should be from consecutive scans within the retention window.

More specifically, this removal step 18 is performed by iterating through the compounds (target compound and the unknowns) that were sorted in the previous step, starting with the target compounds. For each compound, each scan must be examined that is within the retention window. For a given scan within the retention window, it is necessary to remove as much of each ion in the compounds spectra as possible.

For main peaks or ions, all of the ion may be removed. To determine how much may be removed for "necessary" and "unnecessary" ions, the following formula is used:

Ion value=main ion intensity*(relative intensity specified for ion+confidence specified for ion).

If the value of the ion in the scan is less than this calculated amount, then whatever is in the scan will be removed. If the value of the ion is greater than the calculated ion value, then the calculated ion value is subtracted from the amount in the scan. Because whatever can be removed from each scan has already been removed, it is now necessary to determine where exactly the peak begins and ends within the window. Starting at the center of the peak, the algorithm examines other results down each side. If three scans are found in which nothing could be removed, then the edge of the peak has been found.

Also if the algorithm has progressed farther than the peak width (typically 1.5) divided by 3 seconds away from the center, and the amount removed starts to go up (rather than continuously falling) then the peak is over. Scans with nothing removed in the peak are not included. A peak that was stopped because it started to go up will only include half the removed intensity of the scan that is on the edge. Any compounds in which the number of non-zero scans is less than the minimum scans (typically 3) or the area is less than or equal to the minimum area (typically 25) do not get added to the list of removed compounds.

The last step of the first embodiment shown in FIG. 1 is to match unknown compounds 20 in the spectroscopic data to target compounds such that no target compound appears twice. In other words, there may be two or more peaks for the same compound. The peak that is closest to the target compound is selected and the other peaks may be ignored. This step 20 allows the system to return the target compound with information about which target compounds were present, and how confident the system is about the match.

All compounds that were removed using the mass spectra provided in the target list that meet the minimum scan and area requirements are said to "found", and are now not eligible to be matched to any removed unknown compounds. Using the list of values obtained in the correlation step 14, the compounds may now be sorted according to the correlation values, iterating through the list starting with the highest correlation value.

If neither the unknown compound nor the target compound are assigned to any other peaks and designated as "found", and the unknown compound meets all peak area and necessary ion requirements, all of the correlation information and removed data from the unknown is copied to the target compound and the unknown compound is removed from the mass spectra data, and the target compound is designated as "found".

Once this is done, there may now be some target compounds that are not designated as "found". There may also be some unknown compounds that were not matched to any target compounds that may now be returned as peaks that were unidentified. The system may return a list of unknown compounds that did not match very well to any of the supplied target compounds in the target list or in a target library. The user is notified of these unidentified compounds. The algorithm may then be given a larger library to use to identify the still unknown compounds.

In order to increase the accuracy of the first embodiment of the present invention shown in FIG. 1, the developers of the reference or target library that may be associated with the system of the present invention may need to understand that for compounds to be accurately identified, two compounds that have very close retention times (co-elute) should not also have identical main or necessary ions. While the results will usually be accurate, there may be times when the second lowest spectral purity target compound is missed because the lowest one received all the necessary ions.

Figure 2:
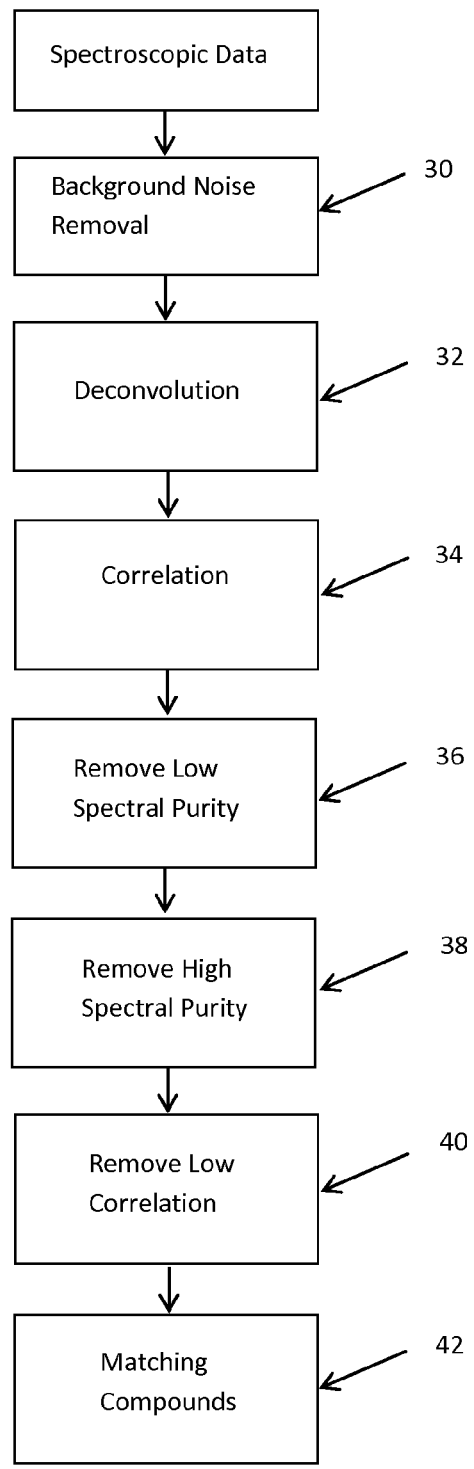
FIG. 2 is a flowchart showing the order of operations of a second embodiment of the present invention.

FIG. 2 is provided as an alternative or second embodiment of the present invention. FIG. 2 is essentially identical to the FIG. 1 through the step of correlation. Thus, the system receives spectroscopic data from which background noise is removed in step 30. The system then performs deconvolution in step 32 to smooth the peaks and then find and group the compounds. The system then performs correlation to identify spectral purity of compounds and a correlation value between combinations of unknown compounds and a target list of compounds in step 34.

However, the second embodiment does not sort through all of the unknown compounds before removing them from further consideration. Instead, the system removes those compounds that are identified, have a low spectral purity in step 36. More specifically, the compounds have a Match Factor that is greater than a MinimumCorrelation (~0.5) on a 0 to 1 scale, and have a low spectral purity defined as being less than a PurityThreshold (~0.8). A low spectral purity means that there are co-eluting compounds that are complicating the mass spectra data. This means that there is likely to be than one compound for those masses, and this step allows those different compounds to be separated from each other. Only those masses that are in the target library should be removed. It is observed that the values selected for the Match Factor and the Spectral Purity may be modified as needed in order to make identification of compounds more accurate.

A possible drawback of performing this step before all the unknown compounds are sorted is that a compound may be eliminated that contains mass spectra of a co-eluting compound that is unintentionally removed.

The next step 38 is defined as removing those compounds from further consideration from the mass spectra data (because they are identified) having a Match Factor that is greater than 0.5, and that have a high spectral purity defined as being greater than 0.8. All the masses that are in the de-convoluted peak as determined above should be removed as long as those masses are in the target list or a reference library. Again, the values selected for the Match Factor and the Spectral Purity may be modified as needed in order to make identification of compounds more accurate.

The next step 40 is to remove from further consideration those masses from the mass spectra data having an inadequate Match Factor defined as being less than MinimumCorrelation. These masses are the unknown compounds in the mass spectra data for the sample being tested. These are the masses that are clearly identifiable as a compound, but do not match any known compounds in the target list or the reference library.

A final step 42 is to check the MinimumArea and Minimum # of Scans on all of the peaks that have been identified as compounds that are in the library, and for those compounds that have now been categorized as unknown compounds. This data may be processed further as necessary, such as using different mass spectra data reference libraries to identify the unknown compounds.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A method of extracting spectra from spectroscopic data obtained by a GC/MS analyzer, the spectroscopic data representing a plurality of different compounds, said method comprising the steps of:
   1) receiving spectroscopic data from a GC/MS analyzer;
   2) removing any signals having a wavelength that is significantly longer than a typical chromatographic peak from the spectroscopic data by processing the spectrographic data in the GC/MS analyzer before the spectrographic data is processed further; and
   3) performing deconvolution on the spectroscopic data using the GC/MS analyzer to thereby find peaks and then group peaks into unknown compounds by first smoothing all peaks using a smoothing filter, and then using the three highest points of each peak of a mass as data points, fitting a parabola to the data points in order to find an intensity of the peak and a time of the maximum point of each peak.

2. The method as defined in claim 1 wherein the method further comprises identifying compounds in the unknown compounds.

3. The method as defined in claim 2 wherein the method further comprises:
   1) providing a target list of identified target compounds;
   2) preparing correlation values for combinations of unknown compound and target compound pairs;
   3) sorting the combinations of unknown compound and target compound pairs by the correlation values;
   4) removing complete ions from the mass spectra data that are identified on the target list; and
   5) matching unknown compounds to target compounds such that no target compound is identified by two different unknown compounds.

4. The method as defined in claim 3 wherein the method further comprises creating a list of unknown compounds that are not on the target list.

5. The method as defined in claim 4 wherein the method further comprises comparing the list of unknown compounds to a different reference library in order to identify more of the unknown compounds.

6. The method as defined in claim 1 wherein the step of background noise removal is performed to smooth spectroscopic data over a broad span so that short duration changes in signal are not fitted when performing deconvolution.

7. The method as defined in claim 1 wherein the step of background noise removal further comprises:
   1) dividing the spectroscopic data into a number of equal subdivisions;
   2) calculating the average time, the mean intensity, and the mean of all non-zero intensities of each subdivision;
   3) calculating the median of all subdivision's means;
   4) calculating the median absolute deviation (MAD) of all subdivision's means;
   5) removing any subdivision whose mean is above the median mean plus the "MAD", or whose mean is zero; and
   6) interpolating a low-pass filter value by using the average time and mean of non-zero intensities of all remaining subdivisions.

8. The method as defined in claim 1 wherein the step of performing deconvolution further comprises grouping peaks by comparing retention times and heights of the peaks.

9. The method as defined in claim 8 wherein the method further comprises:
   1) selecting a highest peak in the spectroscopic data as a main ion;
   2) creating a normal distribution around the main ion;
   3) grouping other peaks with the main ion if the other peaks fall within the normal distribution;
   4) removing the group of ions from further analysis; and
   5) repeating steps 1 through 4 for the next highest peak in the spectroscopic data until all peaks are removed from analysis.

10. The method as defined in claim 9 wherein the method further comprises moving a first ion from a first group of ions to a second group of ions if the first ion falls within the normal distribution of the main ions of the first group and the second group, and the main ion of the second group is found to have a retention that is closer to the first ion.

11. The method as defined in claim 3 wherein the step of preparing correlation values for combinations of unknown compound and target compound pairs further comprises determining match statistics using spectral purity for each of the unknown compounds and a correlation value calculated as a combination of both a mass correlation and a retention time correlation.

12. The method as defined in claim 3 wherein the step of sorting further comprises sorting the unknown compound and target compound combinations, wherein if a spectral purity of a particular unknown compound and target compound combination is below a purity threshold, and the target compound does not have a higher correlation value to a different unknown compound, then mass spectra data for the target compound supplied with a target list is placed on a sorted list.

13. A method of identifying compounds in spectroscopic data obtained by a GC/MS analyzer, the spectroscopic data representing a plurality of different compounds, said method comprising the steps of:
  1) receiving spectroscopic data from a GC/MS analyzer;
  2) removing any signals having a wavelength that is significantly longer than a typical chromatographic peak from the spectroscopic data by processing the spectrographic data in the GC/MS analyzer before the spectrographic data is processed further;
  3) performing deconvolution on the spectroscopic data using the GC/MS analyzer to thereby find peaks and then group peaks into unknown compounds by first smoothing all peaks using a smoothing filter, and then using the three highest points of each peak of a mass as data points, fitting a parabola to the data points in order to find an intensity of the peak and a time of the maximum point of each peak;
  4) providing a target list of identified target compounds;
  5) preparing correlation values for combinations of unknown compound and target compound pairs;
  6) sorting the combinations of unknown compound and target compound pairs by the correlation values;
  7) removing complete ions from the mass spectra data that are identified on the target list; and
  8) matching unknown compounds to target compounds such that no target compound is identified by two different unknown compounds.

14. The method as defined in claim 13 wherein the method further comprises creating a list of unknown compounds that are not on the target list.

15. The method as defined in claim 14 wherein the method further comprises comparing the list of unknown compounds to a different reference library in order to identify more of the unknown compounds.

16. A method of identifying compounds in spectroscopic data representing a plurality of different compounds, said method comprising the steps of:
  1) receiving spectroscopic data from a GC/MS analyzer;
  2) removing any signals having a wavelength that is significantly longer than a typical chromatographic peak from the spectroscopic data by processing the spectrographic data in the GC/MS analyzer before the spectrographic data is processed further;
  3) performing deconvolution on the spectroscopic data using the GC/MS analyzer to thereby find peaks and then group peaks into unknown compounds by first smoothing all peaks using a smoothing filter, and then using the three highest points of each peak of a mass as data points, fitting a parabola to the data points in order to find an intensity of the peak and a time of the maximum point of each peak;
  4) providing a target list of identified target compounds;
  5) preparing correlation values for combinations of unknown compound and target compound pairs;
  6) calculating spectral purity and a match factor on the unknown compounds;
  7) removing from consideration the unknown compounds having a specific match factor and a first spectral purity that are in the target list; and
  8) removing from consideration the unknown compounds having a specific match factor and a spectral purity that is higher than the first and that are in the target list.

17. The method as defined in claim 16 wherein the method further comprises matching unknown compounds to target compounds such that no target compound is identified by two different unknown compounds.

* * * * *